US009795335B2

(12) United States Patent
Merfeld et al.

(10) Patent No.: US 9,795,335 B2
(45) Date of Patent: Oct. 24, 2017

(54) DATA COLLECTION FOR VESTIBULOGRAM CONSTRUCTION

(71) Applicant: Massachusetts Eye and Ear Infirmary, Boston, MA (US)

(72) Inventors: Daniel Michael Merfeld, Lincoln, MA (US); Shomesh Ernesto Chaudhuri, Cambridge, MA (US); Koeun Lim, Somerville, MA (US); Adrian Priesol, Boston, MA (US); Richard Lewis, Brookline, MA (US); Faisal Karmali, Cambridge, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 374 days.

(21) Appl. No.: 14/390,923

(22) PCT Filed: Mar. 15, 2013

(86) PCT No.: PCT/US2013/032619
§ 371 (c)(1),
(2) Date: Oct. 6, 2014

(87) PCT Pub. No.: WO2013/151773
PCT Pub. Date: Oct. 10, 2013

(65) Prior Publication Data
US 2015/0064670 A1    Mar. 5, 2015

Related U.S. Application Data

(60) Provisional application No. 61/679,572, filed on Aug. 3, 2012, provisional application No. 61/621,247, filed on Apr. 6, 2012.

(51) Int. Cl.
*A61B 5/16*    (2006.01)
*A61B 5/18*    (2006.01)
(Continued)

(52) U.S. Cl.
CPC .............. *A61B 5/18* (2013.01); *A61B 5/0057* (2013.01); *A61B 5/16* (2013.01); *A61B 5/4023* (2013.01);
(Continued)

(58) Field of Classification Search
CPC ........... A61B 5/18; A61B 5/0057; A61B 5/16; A61B 5/4023; A61B 5/70; A61B 5/7203; A61B 5/7221; G09B 5/00
See application file for complete search history.

(56) References Cited

U.S. PATENT DOCUMENTS

| 5,942,954 A | 9/1999 | Galliana et al. |
| 2003/0105496 A1 | 6/2003 | Yu et al. |
| 2011/0054356 A1* | 3/2011 | Merfeld ................... A61B 5/00 600/587 |

FOREIGN PATENT DOCUMENTS

| JP | 2007-268164 | 10/2007 |
| WO | WO 2009/129222 | 10/2007 |

(Continued)

OTHER PUBLICATIONS van der Linden, Wim J. "Bayesian item selection criteria for adaptive testing." Psychometrika 63.2 (1998): 201-216.*
(Continued)

*Primary Examiner* — Robert J Utama
*Assistant Examiner* — Kristen Dragon
(74) *Attorney, Agent, or Firm* — Fish & Richardson P.C.

(57) ABSTRACT

The methods, systems, and computer program products described herein enable the amount of information that can be acquired during a defined period of vestibular testing to be significantly increased while also significantly reducing the time required to collect data during such vestibular testing. These objects are achieved by intelligent data collection methods and systems configured to adaptively con-
(Continued)

trol a motion platform in a way that increases the amount of information gleaned from each data collection event and to achieve synergies based on the different types of, and the order of, data analysis and calibration methods used.

23 Claims, 11 Drawing Sheets

(51) Int. Cl.
    *A61B 5/00*     (2006.01)
    *G09B 5/00*     (2006.01)
(52) U.S. Cl.
    CPC .............. *A61B 5/70* (2013.01); *A61B 5/7203* (2013.01); *A61B 5/7221* (2013.01); *G09B 5/00* (2013.01)

(56) References Cited

FOREIGN PATENT DOCUMENTS

| WO | WO 2009/136935 | 11/2009 |
|---|---|---|
| WO | WO 2013/151773 | 10/2013 |

OTHER PUBLICATIONS

Bielinski et al., "How Out-of-Level Testing Affects the Psychometric Quality of Test Scores," Nation Center on Educational Outcomes, Aug. 2000, 15 pages.*
Wichmann and Hill, "The psychometric function: I, Fitting, sampling, and goodness of fit," Percept Psychophys., 2001a, 63:1293-1313, 2001.*
'Wikipedia' [online] "Maximum likelihood," May 2014, [retrieved on Nov. 14, 2014]. Retrieved from the Internet: http://en.wikipedia.org/wiki/Maximum likelihood#Higher-order-.properties, 14 pages.
Benson et al., "Thresholds for the detection of the direction of whole-body, linear movement in the horizontal plane," Aviat Space Environ Med., 1986, 57:1088-96.
Benson et al., "Thresholds for the Perception of Whole Body Angular Movement About a Vertical Axis," Aviat Space Environ Med., Mar. 1989, 60:205-213.
Berg et al., "Deviance Information Criterion for Comparing Stochastic Volatility Models," J Business Economic Statistics, 2004, 22:107-120.
Bertolini et al., "Velocity storage contribution to vestibular self-motion perception in healthy human subjects," J Neurophysiol., 2011, 105:209-223.
Bronstein et al., "Reduced self-motion perception in patients with midline Cerebellar lesions," Neuroreport, 2008, 19:691-693.
Burnham and Anderson, "Multimodel Inference: Understanding AIC and BIC in Model Selection," Sociological Meth Res., 2004, 33:261-304.
Celeux et al., Centre de recherche en Economie et,statistique (2003) "Deviance information criteria for missing data models," INSEE, Paris, 30 pages.
Clark and Graybiel, "Perception of the postural vertical in normals and subjects with labyrinthine defects," J Exp Psychol., 1963, 65:490-494.
Cohen et al., "Spatial orientation of the angular vestibule-ocular reflex," J Vestib Res., 1999, 9:163-172.
Cohen et al., "Velocity storage, nystagmus, and visual-vestibular interactions in humans," Ann NY Acad Sci., 1981, 374:421-33.
Crane and Demer, "Human Horizontal Vestibulo-Ocular Reflex Initiation: Effects of Acceleration, Target Distance, and Unilateral Deafferentation," J Neurophysiology, 1998, 80:1151-1166.
Crane, "Fore-ail translation aftereffects," Exp Brain Res., 2012, 219:477-487.
Diekmann et al., "Maintaining spatial body alignment on a rotating platform by means of active counter-circling: role of vestibular and podokinesthetic afferent," Exp Brain Res., 2004, 158:504-518.

Dimitri et al., "Multivariate vestibular testing: laterality of unilateral Meniere's disease," J Vestib Res., 2001, 11:405-412.
Fernandez and Goldberg, "Physiology of peripheral neurons innervating otolith organs of the squirrel monkey. III. Response Dynamics," J Neurophysiol., 1976, 39:996-1008.
Firth, "Bias reduction of maximum likelihood estimates," Biometrika, 1993, 80:27-38.
Foster and Bischof, "Thresholds from psychometric functions: superiority of bootstrap to incremental and probit variance estimators," Psychol Bull., 1991, 109:152-159.
Goldberg and Fernandez, "Physiology of peripheral neurons innervating semicircular canals of the squirrel monkey. I. Resting discharge and response to constant angular accelerations," J Neurophysiol., 1971b, 34:635-60, 1971.
Goldberg and Fernandez, "Physiology of peripheral neurons innervating semicircular canals of the squirrel monkey. III. Variations among units in their discharge properties," J Neurophysiol., 1971a, 34:676-84, 1971.
Golding, "Motion sickness susceptibility questionnaire revised and its relationship to other forms of sickness," Brain Res Bulletin, 1998, 47:507-16.
Grabherr et al., "Vestibular thresholds for yaw rotation about an earth-vertical axis as a function of frequency," Exp Brain Res., Apr. 2008, 186(4):677-681.
Graybiel et al., "The law of the otolith organs," Fed Proc., 1946, 5:35.
Green and Angelaki, "Resolution of sensory ambiguities for gaze stabilization requires a second neural integrator," J Neurosci., 2003, 23:9265-9275.
Haburcakova et al., "Frequency dependence of vestibuloocular reflex thresholds," J Neurophysiol., 2012, 107:973-983.
Hall, "Hybrid adaptive procedure for estimation of psychometric functions," J Acoust Soc Am., 1981, 69:1763-1769.
Ifediba et al., "The role of 3-canal biomechanics in angular motion transduction by the human vestibular labyrinth," Ann Biomed Eng., 2007, 35:1247-63.
Jakel and Wichmann, "Spatial tour-alternative forced-choice method is the preferred psychophysical method for naive observers," J Vis., 2006, 6:1307-1322.
Kaernbach, "Slope bias of psychometric functions derived from adaptive data," Percept Psychophys, 2001, 63:1389-1398.
Klein, "Measuring, estimating, and understanding the psychometric function: a commentary," Percept Psychophys, 2001, 63:1421-1455.
Knoblauch and Maloney, "Estimating classification images with generalized linear and additive models," J Vis., 2008, 8:1-19.
Kosmidis, "Bias reduction in exponential family nonlinear models," PhD, thesis, Dept. of Statistics, Univ, Warwick, England, 2007, 160 pages.
Leek et al., "Estimation of psychometric functions from adaptive procedures," Percept Psychophys, 1992, 51:247-256.
Leek MR, "Adaptive procedures in psychophysical research," Percept Psychophys, 2001, 63:1279-92.
Lim and Merfeld, "Erratum to: Signal Detection Theory and Vestibular Perception: II, Fitting Perceptual Thresholds as a Function of Frequency," Exp Brain Res., 2013, 224:501.
Lim and Merfeld, "Signal Detection Theory and Vestibular Perception: II, Fitting Perceptual Thresholds as a Function of Frequency," Exp Brain Res., 2012, 222:303-320.
Lim et al., "Self-motion direction-detection thresholds for whole body roll tilts about an earth-horizontal axis," ARO, 2009, Abstr 103, Session D15: Poster, 1 page.
Mann et al., "The perception of the vertical; visual and non-labyrinthine cues," J Exp Psychol., 1949, 39:538-547.
McKee et al., "Statistical properties of forced-choice psychometric functions: Implications of probit analysis," Atten Percept Psychophys, 1985, 37:286-298.
Merfeld et al., "Vestibular perception and action employ qualitatively different mechanisms. I. Frequency response of VOR and perceptual responses during Translation and Tilt," J Neurophysiol., 2005a, 94:186-98, 2005.

(56) References Cited

OTHER PUBLICATIONS

Merfeld et al., "Vestibular perception and action employ qualitatively different mechanisms. II. VOR and perceptual responses during combined Tilt & Translation," J Neurophysiol., 2005b, 94:199-205, 2005.

Merfeld, "Signal detection theory and vestibular thresholds: 1. Basic theory and practical considerations," Exp Brain Res., 2011, 210:389-405.

MOOG Systems Group. Series 6DOF2000E Electric Motion Platform. 2 pages, Feb. 2008.

Morgan et al., "Observers can voluntarily shift their psychometric functions without losing sensitivity," Atten Percept Psychophys., 2012, 74:185-193.

Neuhauser et al., "The interrelations of migraine, vertigo and migrainous vertigo," Neurol., 2001, 56:436-441.

Okada et al., "Vestibular perception of angular velocity in normal subjects and in patients with congenital nystagmus," Brain, 1999, 122 (Pt 7):1293-1303.

Peterka et al., "Age-related changes in human vestibulo-ocular and optokinetic reflexes: pseudorandom rotation tests," J Vestib Res., 1990, 1:61-71.

Raphan et al., "Velocity storage in the vestibulo-ocular reflex arc (VOR)," Exp Brain Res., 1979, 35:229-48.

Roditi and Crane, "Directional asymmetries and age effects in human self-motion perception," J Assoc Res Otolaryngol., 2012, 13:381-401.

Roditi and Crane, "Suprathreshold asymmetries in human motion perception," Exp Brain Res., 2012, 219:369-379.

Sinha et al., "Perception of self motion during and after passive rotation of the body around an earth-vertical axis," Prog Brain Res., 2008, 171:277-281.

Soyka et al., "Modeling direction discrimination thresholds for yaw rotations around an earth-vertical axis for arbitrary motion profiles," Exp Brain Res., 2012, 220:89-99.

Soyka et al., "Predicting direction detection thresholds for arbitrary translational acceleration profiles in the horizontal plane," Exp Brain Res., 2011, 209:95-107.

Taylor and Creelman, "PEST: Efficient estimates on probability functions," J Acoust Soc Am., 1967, 41:782-787.

Treutwein and Strasburger, "Fitting the psychometric function," Percept Psychophys., 1999, 61:87-106.

Walsh, "Role of the vestibular apparatus in the perception of motion on a parallel swing," J Physiol., 1961, 155:506-513.

Wedderburn, "On the existence and uniqueness of the maximum likelihood estimates for certain generalized linear models," Biometrika, 1976, 63:27-32.

Wichmann and Hill, "The psychometric function: I. Fitting, sampling, and goodness of fit," Percept Psychophys., 2001a, 63:1293-1313, 2001.

Wichmann and Hill, "The psychometric function: II. Bootstrap-based confidence intervals and sampling," Percept Psychophys., 2001b, 63:1314-1329, 2001.

Yssaad-Fesselier and Knoblauch, "Modeling psychometric functions R," Behav Res Methods, 2006, 38:28-41.

Zupan and Merfeld, "Interaural self-motion linear velocity thresholds are shifted by roll vection," Exp Brain Res., 2008, 191:505-11.

\* cited by examiner

DATA COLLECTION FOR VESTIBULOGRAM CONSTRUCTION

CROSS REFERENCE TO RELATED APPLICATIONS

This application is being filed pursuant to 35 U.S.C. §371(c) from the PCT Application No. PCT/US2013/032619, filed Mar. 15, 2013, which claims priority to U.S. Provisional Application 61/621,247 filed on Apr. 6, 2012, and U.S. Provisional Application 61/679,572, filed on Aug. 3, 2012. The entire contents of the above applications are incorporated herein by reference.

STATEMENT OF GOVERNMENT RIGHTS

This work was supported in part by NIH/NIDCD grant DC04158, NIH grant R56DC012038, and NIH shared equipment grant 1S10RR028832. The United States government may have certain rights in the invention.

FIELD OF DISCLOSURE

This disclosure relates to assessment of vestibular function, and in particular, to vestibulograms.

BACKGROUND

In an effort to assess a subject's vestibular system, it is often useful to obtain a vestibulogram showing vestibular threshold as a function of motion frequency.

Acquisition of data to create a vestibulogram can be time consuming. The subject typically sits on a motion platform and presses buttons to signal his perception of motion. Since only motion perception that results from the vestibular system is of interest, all other motion cues must be suppressed. Thus, the subject sits in the dark to avoid visual cues, wears headphones playing white noise to avoid audio cues arising from the sound of the machinery, and gloves to avoid tactile cues arising from moving air.

Because data is collected across numerous motion frequencies and amplitudes, the subject endures this experience of almost complete sensory isolation for several hours. During this period, the subject must provide enough sustained attention, so that he can correctly indicate his perception for each motion. He cannot pass the time by dozing or daydreaming. Such lapses of attention would impair data acquisition.

From a subject's point of view, the clinical experience of testing one's vestibular function is far more grueling than that of listening to sounds for half an hour to obtain an audiogram, or reading an eye chart to assess one's visual acuity. From a clinician's point of view, the time taken to carry out the test reduces the number of tests that can be given in a year. As a result, many people suffering from vestibular dysfunction must wait months to even be tested.

SUMMARY

The methods and systems described herein enable the amount of information that can be acquired during a defined period of vestibular testing to be significantly increased while also significantly reducing the time required to collect data during such vestibular testing. These objects are achieved by intelligent data collection methods and systems configured to adaptively control a motion platform in a way that increases the amount of information gleaned from each data collection event and to achieve synergies based on the different types of, and the order of, data analysis and calibration methods used.

The disclosure features systems, methods and computer readable storage devices encoded with computer readable instructions, that are directed to techniques for reducing overall time for a test to estimate one or more parameters related to a psychometric function of a subject. The techniques include administering one or more trials to the subject, wherein for each trial, the testing device is configured to provide a motion stimulus to the subject. The motion stimulus corresponds to a particular test parameter. The techniques also include receiving a response indicative of a perception of the motion stimulus, and estimating the one or more test parameters based on the received response. One or more of the following are implemented using the techniques described herein. The motion stimulus can be adaptively selected. Biases associated with the one or more test parameters can be reduced. One or more fit parameters related to a unified data set obtained from data sets corresponding to multiple test parameters, can be obtained. A time duration between administering the one or more trials can be reduced, without affecting accuracy of the estimates of the one or more parameters. The motion stimuli can be synchronized with a cardiac cycle of the subject.

The motion stimulus can be preceded by providing a distracting motion along a direction different from a direction of the motion stimulus. The response can include a confidence rating provided by the subject, wherein the confidence rating is associated with the subject's confidence level related to the perception of the motion stimulus. The time duration between administering the one or more trials can be reduced by providing a reorientation aid by rapidly switching a light source on and off to temporarily illuminate a reference object. The motion stimuli can be synchronized with a cardiac phase of the subject by providing each of the motion stimuli at a particular portion of the cardiac cycle of the subject. The various techniques described above can be implemented using one or more combinations of the following.

In one aspect, the disclosure includes systems for estimating a subject's vestibulogram. Such systems include a motion platform for supporting a subject, the motion platform configured to execute motion profiles, and a special purpose computer programmed to obtain a first estimate of a parameter vector of the subject's psychometric function based on information indicative of a subject's perception of motion in response to a first motion profile set, and to adaptively select a subsequent motion profile based at least in part on the first estimate.

In some implementations, the computer is programmed to select the subsequent motion profile to reduce uncertainty in the estimate. Among these are those in which the computer is programmed to select the subsequent motion profile to maximize reduction of uncertainty in the estimate. Among these latter implementations are those in which the computer is programmed to select the subsequent motion profile based at least in part on Fisher information associated with the estimate.

In other implementations, the computer is further configured to cause the motion platform to execute one or more motion profiles, to collect information indicative of the subject's perception of motion in response to each of the motion profiles, and, based at least in part on the first estimate and the information, to generate a second estimate, the second estimate having less uncertainty than the first estimate.

Additional implementations include those in which the parameter vector includes a component defining a value at which the psychometric function indicates that the subject's perception of motion is as likely to be incorrect as it is to be correct, and those in which the parameter vector includes a component that defines a spread about a point at which the psychometric function indicates that the subject's perception of motion is as likely to be incorrect as it is to be correct.

In some implementations, the subsequent motion profile defines a motion having a frequency that differs from a frequency of a preceding motion profile. In others, the subsequent motion profile defines a motion having an amplitude that differs from an amplitude of a preceding motion profile.

Implementations of the systems and techniques also include those in which the computer adaptively selects a subsequent motion profile. These include implementations in which the computer is programmed to adaptively select a subsequent motion profile based on a predefined relationship between the first estimate of a parameter vector and a frequency of motion, and implementations in which the computer is programmed to adaptively select a subsequent motion profile based by weighting stimuli amplitudes utilized at a frequency of a preceding motion profile by a high-pass filter transfer function having a subject-specific cut-off frequency.

In additional implementations, the computer is further programmed to make certain corrections. In some of these, the special purpose computer is further programmed to correct a bias in an estimate of the first estimate of the parameter vector based on a generalized linear model of the information indicative of the subject's perception of motion in response to the first motion profile set. In others, the computer is programmed to correct for lapses in the subject's attention by identifying outlier data and eliminating the outlier data prior to obtaining the first estimate. Among these are those in which the computer is configured to determine an extent to which the outlier data changes the first estimate of the parameter vector.

In another aspect, the disclosure features an apparatus for estimating a subject's vestibulogram. Such an apparatus includes a motion platform for supporting a subject, the motion platform being configured to execute motion profiles, and a special purpose computer programmed to obtain a first estimate of a parameter vector of the subject's psychometric function based on information indicative of the subject's perception of motion.

Among these implementations are those in which the special purpose computer is configured to obtain the first estimate based on the subject's perception of motion at a single frequency and those in which the special purpose computer is configured to obtain the first estimate based on the subject's perception of motion at a more than one frequency.

Among these implementations are those in which the special purpose computer is configured to iteratively use the subject's responses to one or more motion profiles to adaptively select a subsequent motion profile. Another aspect of the invention includes an apparatus for estimating a subject's vestibulogram. Such an apparatus includes a motion platform for supporting a subject and configured to execute motion profiles, and a special purpose computer programmed to select a subsequent motion profile based on an expected extent to which information indicative of the subject's perception of the motion profile would improve an estimate of a parameter vector of the subject's psychometric function.

In another aspect, the disclosure features a method for estimating a subject's vestibulogram. Such a method includes supporting a subject on a motion platform, selecting a motion profile based on an expected extent to which information indicative of the subject's perception of the motion profile would improve an estimate of a parameter vector of the subject's psychometric function, and executing the selected motion profile.

In some practices, the parameter vector includes an estimate of at least one of a roll vestibular bias and a tilt vestibular bias. In such cases, the method further includes predicting existence of vestibular migraine based at least in part on the estimate.

In another aspect, the disclosure features a method for estimating a subject's vestibulogram. Such a method includes supporting a subject on a motion platform, causing the platform to execute motion profiles, and obtaining a first estimate of a parameter vector of the subject's psychometric function based on information indicative of the subject's perception of motion.

Among the practices of the above method are those that comprise iteratively using the subject's responses to one or more motion profiles to adaptively select a subsequent motion profile.

In another aspect, the disclosure features a manufacture comprising a nontransitory and tangible computer-readable medium having encoded thereon software for estimating a vestibulogram of a subject supported on a motion platform the software comprising instructions for causing the platform to execute motion profiles, and obtaining a first estimate of a parameter vector of the subject's psychometric function based on information indicative of the subject's perception of motion.

In some implementations, the software further comprises instructions for iteratively using the subject's responses to one or more motion profiles to adaptively select a subsequent motion profile.

In another aspect, the disclosure features a manufacture comprising a tangible and non-transitory computer readable medium having encoded thereon software for estimating a vestibulogram of a subject supported on a motion platform, the software including instructions for selecting a motion profile based on an expected extent to which information indicative of the subject's perception of the motion profile would improve an estimate of a parameter vector of the subject's psychometric function, and executing the selected motion profile.

In another aspect, this disclosure presents methods for obtaining a bias-reduced estimate of a fit parameter representing psychometric data. The methods include obtaining a set of values that represent psychometric data, and determining at least one fit parameter, such as a standard deviation or mean of a distribution, that represents the obtained set of values. The methods also include estimating a bias quantity associated with the at least one fit parameter, and subtracting the bias quantity from the at least one fit parameter to obtain a bias-reduced estimate of the fit parameter.

In another aspect, this disclosure presents systems for obtaining a bias-reduced estimate of a fit parameter representing psychometric data. The systems can include one or more software and/or hardware modules that can be implemented using, for example, a memory and a processor. The processor is configured to obtain a set of values that represent psychometric data, and determine at least one fit parameter, such as a standard deviation or mean, which represents the obtained set of values. The processor can also be configured to estimate a bias quantity, such as an upward bias or downward bias associated with the at least one fit parameter, and subtract the bias quantity from the at least one fit parameter to obtain a bias-reduced estimate of the fit parameter.

In another aspect, this disclosure presents methods for estimating a fit parameter that represents a set of values, e.g., values representing responses of a subject in a psychometric test. The methods include determining at least one fit parameter that represents a distribution of a set of values, estimating a bias quantity associated with the at least one fit parameter, and subtracting the bias quantity from the at least one fit parameter to obtain a bias-reduced estimate of the fit parameter. The methods also include scaling the bias-reduced estimate of the at least one fit parameter by a scale-factor that is less than unity to obtain a final estimate of the fit parameter.

In another aspect, this disclosure presents systems for estimating a fit parameter that represents a set of values. The systems include a memory and a processor. The processor is configured to determine at least one fit parameter that represents a distribution of a set of values, estimate a bias quantity associated with the at least one fit parameter, and subtract the bias quantity from the at least one fit parameter to obtain a bias-reduced estimate of the fit parameter. The processor is further configured to scale the bias-reduced estimate of the at least one fit parameter by a scale-factor that is less than unity to obtain a final estimate of the fit parameter.

In another aspect, this disclosure presents methods for estimating a fit parameter that represents a set of values. The methods include obtaining a plurality of sets of values, wherein each set corresponds to a different value of a test parameter, such as a reciprocal of the time duration (also referred to as frequency) for which a stimulus is applied in each trial to obtain a given set of values, and each value is included in a predetermined set of discrete values. The methods also include scaling values from at least one of the plurality of sets using a corresponding scaling function such that the scaled values from the at least two sets of the plurality of sets are mapped onto a unified set, and determining at least one fit parameter that represents a distribution of the scaled values in the unified set.

In another aspect, this disclosure presents systems for estimating a fit parameter that represents a set of values, e.g., in conjunction and/or in communication with a test device, such as a motion platform. The systems include at least a memory, and a processor that is configured to obtain a plurality of sets of values, wherein each set corresponds to a different value of a test parameter and each value is included in a predetermined set of discrete values. The processor is also configured to scale values from at least one of the plurality of sets using a corresponding scaling function such that the scaled values from the at least two sets of the plurality of sets are mapped on to a unified set, and determine at least one fit parameter that represents a distribution of the scaled values in the unified set.

In another aspect, this disclosure presents computer readable storage devices having encoded thereon computer readable instructions. The instructions, when executed by a processor, cause a processor to perform one or more operations. The operations include obtaining a set of values that represent psychometric data, and determining at least one fit parameter that represents the obtained set of values. The operations also include estimating a bias quantity associated with the at least one fit parameter, and subtracting the bias quantity from the at least one fit parameter to obtain a bias-reduced estimate of the fit parameter.

In another aspect, this disclosure presents computer readable storage devices having encoded thereon computer readable instructions. The instructions, when executed by a processor, cause a processor to perform one or more operations. The operations include determining at least one fit parameter that represents a distribution of a set of values, and estimating a bias quantity associated with the at least one fit parameter. The operations also include subtracting the bias quantity from the at least one fit parameter to obtain a bias-reduced estimate of the fit parameter, and scaling the bias-reduced estimate of the at least one fit parameter by a scale-factor that is less than unity to obtain a final estimate of the fit parameter.

In another aspect, this disclosure presents additional computer readable storage devices that have encoded thereon computer readable instructions. The instructions, when executed by a processor, cause a processor to perform one or more operations. The operations include obtaining a plurality of sets of values, wherein each set corresponds to a different value of a test parameter and each value is included in a predetermined set of discrete values, and scaling values from at least one of the plurality of sets using corresponding scaling functions such that the scaled values from the at least two sets of the plurality of sets are mapped on to a unified set. The operations also include determining at least one fit parameter that represents a distribution of the scaled values in the unified set.

Implementations can include any combination or sub-combination of the following.

A psychometric test can be administered to a subject and responses of the subject can be measured to obtain the set of values. The responses of the subject can be measured for stimuli corresponding to a plurality of values of a test parameter. The responses to different values of the test parameter can be scaled using a corresponding scaling function to obtain the set of values that represent the psychometric data. The psychometric test can include providing a stimulus to the subject. The test parameter can be a reciprocal of a time duration for which the stimulus is provided. The psychometric test can include an adaptive sampling procedure. The stimulus can be provided to the subject for a predetermined number of times to measure the responses of the subject. The number of values in the set of values can be less than or equal to 200, e.g., less than 150, 100, 75, 50, or 25. Given the new systems and methods, fit parameters can be accurately estimated from a relatively small number of values such as test results.

The distribution of the psychometric data can be represented as a cumulative distribution function. The cumulative distribution function can be a cumulative Gaussian distribution. Each of the responses of the subject can be represented as one of a predetermined set of discrete values. Each of the responses of the subject can be binary. The one or more fit parameters can be determined using a generalized linear model (GLM) fit.

The one or more fit parameters can be determined using a numerical maximum-likelihood method. The bias quantity can represent a first order asymptotic bias. A psychometric test can be administered to the subject by positioning the subject on a motion platform configured to execute motion profiles, and obtaining a first estimate of a parameter vector of the subject's psychometric function based on information indicative of the subject's perception of motion in response to a first motion profile set.

A subsequent motion profile can be subsequently selected based at least in part on the first estimate. The subsequent motion profile can be selected to reduce uncertainty in the estimate. The subsequent motion profile can be selected to maximize reduction of uncertainty in the estimate. The subsequent motion profile can be based at least in part on Fisher information associated with the estimate.

Lapses in the subject's attention can be corrected by identifying outlier data and eliminating the outlier data prior to obtaining the first estimate. The set of discrete values can include binary values. The binary values can represent binary responses of a subject. The binary responses can be obtained by providing a stimulus to the subject. The stimulus can be a motion stimulus.

The set of values can be obtained from a testing apparatus that can include, for example, a motion platform for supporting a subject. The processor can be configured to communicate with the testing apparatus over a wired or wireless link and send instructions to and receive information from the testing apparatus. The motion platform can be configured to execute motion profiles. The processor can be programmed to obtain a first estimate of a parameter vector of the subject's psychometric function based on information indicative of a subject's perception of motion in response to a first motion profile set, and to adaptively select a subsequent motion profile based at least in part on the first estimate. The processor can also be configured to provide to the testing apparatus with one or more control signals to control, for example, selection of a motion profile.

The scaling functions can be characterized by a set of one or more scaling parameters. A psychometric test can be administered to a subject. Responses of the subject can be measured to obtain the plurality of sets of values. For a given set of discrete values, the responses of the subject can be obtained by providing stimuli to the subject. Value of the test parameter can be computed as a reciprocal of a time duration for which an individual stimulus is provided. The stimuli can include a series of motion stimuli.

One or more of the methods described herein are useful in characterizing vestibuloocular reflex (VOR) responses and/or thresholds.

As used herein, the tangible non-transitory computer readable media expressly excludes transitory signals.

These and other features of the invention will be apparent from the following detailed description and the accompanying figures.

DETAILED DESCRIPTION

Figure 1:
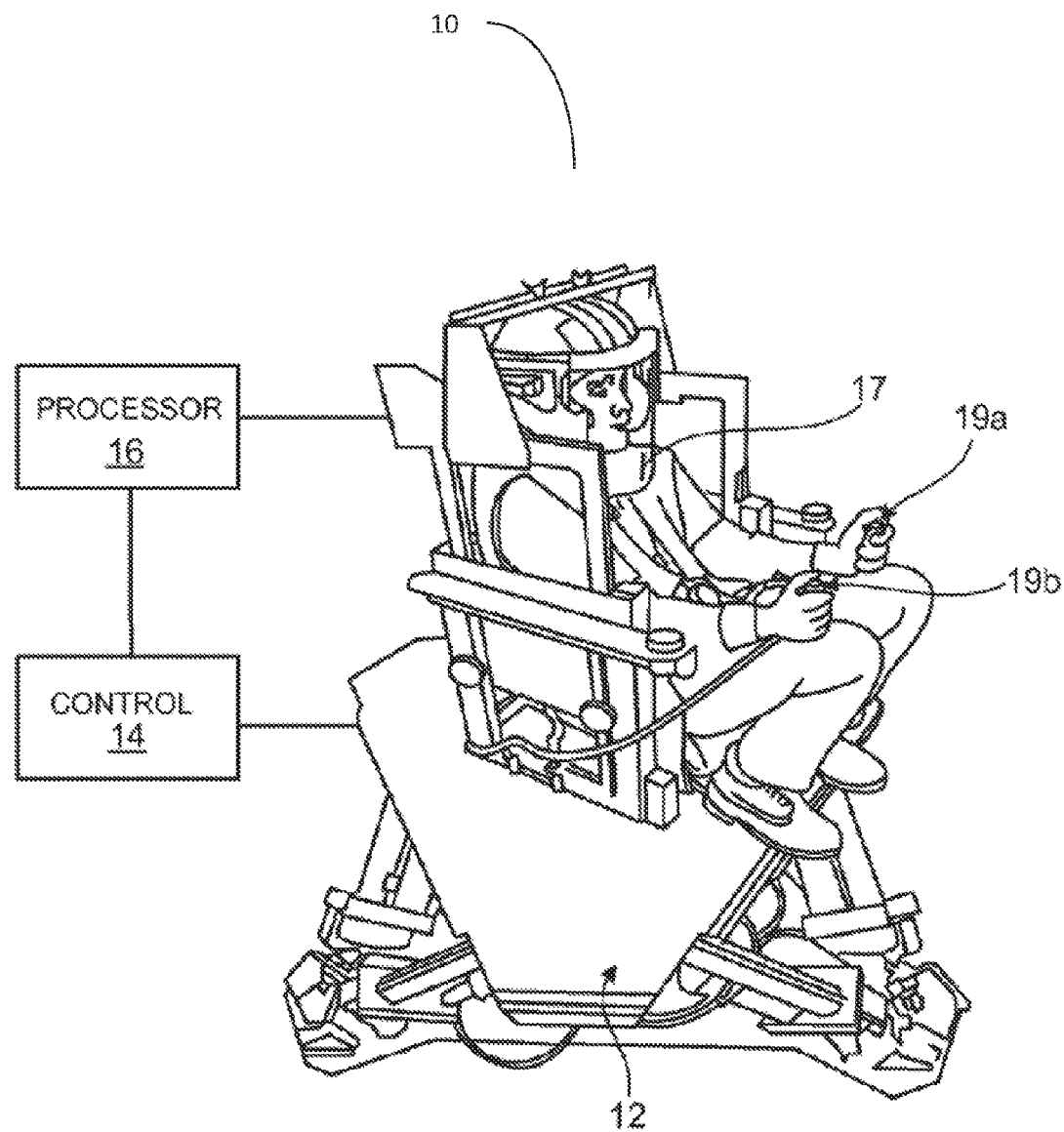
FIG. 1 is a representation of a vestibulogram data collection system.

Human behavior can be assayed using psychophysical methods. For example, human behavior can be quantitatively represented using estimated fit parameters that characterize human psychophysical responses to a psychometric test. Quantitative assays that are robust, accurate, precise, and efficient, can be used for diagnostic purposes. Efficiency can be determined as, for example, a function of time or number of trials used in a psychometric test needed to yield a robust, accurate, and precise estimate of the fit parameter(s) that characterize psychophysical responses of a human subject.

For example, vestibular psychophysical responses may be represented using fit parameters. A subject is moved (e.g., translated or rotated, or a combination of both) with respect to a head centered coordinate system defined by orthogonal axes x, y, and z. The subject can be translated along the z axis, translated along the y axis, rotated about the y-axis ("yaw rotation"), or rotated about the x-axis ("roll tilt"). For these, and other types of motion defined in the head centered coordinate system, the subject undergoes motion stimuli, each motion stimulus having a characteristic duration or frequency (f) and a characteristic amplitude (V). The subject's responses to the motion stimuli can be used to determine the subject's vestibular perceptual thresholds, (f, V) at which the subject can barely detect or recognize motion. However, accurate and precise determinations of vestibular thresholds using existing methods require many motion stimuli across multiple frequencies (e.g., 5 frequencies) and testing can take up to two hundred minutes per motion type (e.g., z-axis translation, y-axis translation, yaw rotation, or roll tilt). The methods, systems, and computer programs described in this application reduce testing time more than ten fold, for example, to less than or about 19, 18, 17, 16, 15, 14, 13, 12, 11, 10, 9, 8, 7, 6, or 5 minutes, without loss of accuracy or precision.

For example, this document discloses methods, systems and computer program products related to a bias reduction technique that can be used to reduce a bias associated with one or more estimated fit parameters. For example, given a certain number of trials to acquire a set of values that represent the responses of a subject to a psychometric test, the bias-reduction technique described here can be used to reduce the bias on one or more estimated parameters such as the standard deviation (referred to as $\sigma$) or mean (referred to as $\mu$) of the set of values. In some implementations, the set of values represents the subject's responses to motion stimuli at a single frequency (f) and for one motion type (e.g., z-axis translation, y-axis translation, yaw rotation, or roll tilt). In some implementations, a single fit of a psychometric function can be used for this purpose. In some implementations, the technique described here can yield a more accurate estimate of $\sigma$ without affecting the variance of the parameter or the accuracy and precision of the estimate for $\mu$.

In some implementations, bias reduction can be performed, by calculating the first-order bias on an estimated parameter (e.g., $\sigma$) and subtracting the calculated bias from the estimated parameter. In some implementations, a scale factor may also be applied on the bias-reduced parameter estimate to further reduce the bias. Because the scale factor is applied after subtracting the first-order bias correction, the scale factor is less than unity, thereby reducing the variation of the parameter estimate while also reducing the parameter bias.

This document also describes methods, systems and computer program products related to a technique that can be used to map datasets corresponding to different parameters (for example, data sets obtained for different test parameters in a psychometric test) on to a unified dataset. This technique can be used, for example, to automatically analyze data at real-time (e.g., when testing at each test parameter, such as a given frequency, is complete) without waiting until data corresponding to all the different test parameters are obtained.

Also described here are methods, systems and computer program products related to a technique for choosing the stimuli to provide to an individual subject undergoing a psychometric test. The chosen stimuli can be expected to yield maximal information from the psychometric data collected using the stimuli. In some implementations, this technique can be used in implementing an automated system that administers a psychometric test to a subject with zero or minimal intervention from a human operator.

The different techniques described in this document can be used independently or in combinations with one another of two, three, or more of the various techniques and methods described herein. Such combinations are new and can provide synergistic results compared to what those of skill in this field might have expected upon combining such techniques. For example, choosing a series of stimuli for the next test can be based on a bias-reduced estimate of a parameter representing the subject's psychometric function. In another example, the bias-reduced estimate can be generated based on a unified dataset obtained by appropriately scaling a number of different datasets (e.g., each corresponding to a different test parameter). In some implementations, the techniques described here can be implemented as an integrated system that includes a testing apparatus including, for example, a motion device, a motion controller, and a programmable computer. In some implementations, the techniques can be implemented in a system or computer program product that interacts with an existing testing apparatus or motion device/controller to at least partially automate the apparatus or device.

In such cases, the system can be in communication with the test apparatus to send instructions to the test device, and receive data from the test device representing responses of a human subject to stimuli related to a psychometric test. The system can be configured to analyze the data in accordance with one or more techniques described in this document. The system can also be configured to provide the test apparatus with one or more control signals. For example, the system can analyze the data received from the test apparatus to compute a bias-reduced parameter estimate and then provide a control signal representing the next stimulus or motion profile in accordance with the computed bias-reduced estimate. In some implementations, a motion profile includes a single motion stimulus. In some implementations, after a human operator prepares a subject for the test, the automated system can be configured to perform one or more operations such as selecting the motion stimuli, administering the selected motion stimuli, accumulating the responses from the subject, and deciding when to end the test session. The system can also be configured to analyze the data and prepare the test report summarizing the test results.

Example of a Vestibular Testing System

As shown in FIG. 1, a data-collection system 10 features a motion platform 12, a controller 14 for controlling the motion of the platform 12, and a specially-programmed processor 16 for receiving information about a subject's perception and using that information to instruct the controller 14 on how to control the motion, e.g. translation and/or rotation, of the motion platform 12. The motion platform 12 can be capable of providing motion in various directions (e.g., 3 rotational and 3 translational directions). The motion platform 12 can include a chair and a restraint system 17 (e.g., a five-point harness, and an adjustable head restraint). The motion platform 12 can also include one or more input devices (e.g., the buttons 19a and 19b) to receive input on a subject's perception of motion. In some implementations, the responses can be received via a wired or wireless handheld device such as a tablet computer or smartphone. The handheld device can be configured to receive the responses from the subject and provide the responses to the processor 16.

The subject can indicate his perception, for example, by pressing certain buttons, or touching predetermined locations on a touchscreen input device. In some implementations, the input device can include motion sensors, accelerometers, or gyroscopes, thereby allowing the user to simply tilt the device in various directions to record their responses. In some implementations, the subject can input his perception of a motion by swiping the display of the input device. For example, the subject can swipe his fingers on the display to the left to indicate that he perceived a motion to his left direction. In some implementations, the input device can be configured to accept additional input from the subject, for example, a confidence rating associated with the response provided.

Specifically, the processor 16 is configured to instruct the controller 14 to cause execution of those motions for which expected information about a subject's perception of those motions would most contribute to improving an estimate of a subject's vestibular threshold. Such an estimate can be used to construct a vestibulogram, which shows the subject's vestibular threshold at different frequencies.

Data provided by the vestibulogram is useful for assisting a clinician in assessing the condition of a subject's vestibular system. For example, such data can be used to provide a more sensitive measurement of vestibular hypofunction than what is currently available, for localizing a pathology responsible for transient symptoms, such as episodic vertigo, and as an assay of hypofunction of, for example, the utricular otolith organ, an assay for which no clinically effective procedure exists.

As one example, it is known that subjects with vestibular migraine have roll tilt vestibular thresholds that are somewhat lower than those of the general population. Additional examples are discussed in the reference: Lewis R. F., Priesol A. J., Nicoucar K., Lim K., Merfeld D. M., *Abnormal motion perception in vestibular migraine*, The Laryngoscope. 2011; 121(5):1124-5, the entire content of which is incorporated herein by reference. The availability of a clinically practical measure of such thresholds eliminates the current practice of indirect diagnosis by elimination of all other causes, typically through the use of various expensive imaging procedures.

The motion platform 12 moves the subject along a trajectory in a spatial coordinate system while following a velocity profile. The velocity profile relates the magnitude of velocity to time. At the beginning and end of the motion, the magnitude of the velocity is zero. At some point in between, the velocity reaches a maximum magnitude, referred to herein as "peak velocity." In many applications, the velocity profile is one cycle of a such a velocity oscillation. The reciprocal of the period of this sine wave is referred to herein as "the motion frequency."

The motion itself can be a translation along a line, which for convenience is along one of three orthogonal axes, or a rotational motion, such as a pitch, roll, or yaw. The motion can also be a combination of any of the foregoing, however such motions can tend to complicate data analysis.

As noted above, the shape of the velocity profile is sinusoidal. However, other shapes are possible, such as those defined by superpositions of weighted and/or time-shifted components.

In some implementations, the system 10 can include a Vestibulo-Ocular Reflex (VOR) detector configured to capture data representing the VOR response of a subject. Many such VOR detectors are known, including semi-invasive detectors, such as coils that are implanted in the eye, and noninvasive detectors, such as coils embedded in contact lenses that are placed on the eye, cameras or machine vision systems that detect eye movement, and electro-oculographic systems.

In some implementations, vestibular tests can be adapted for VOR analysis to use the vestibulo-ocular reflexes as an indicator of the subject's perception of motion. For example, the subject can be positioned on the motion platform 12 and be subjected to the motion tests. However, instead of pushing buttons 19 at the end of each motion to indicate the perception of motion, the direction of the subject's reflexive eye movements can be measured and compared to the direction of the motion applied. The result of the comparison after each motion list is recorded on a feedback list and analyzed using methods such as described herein.

Figure 2:
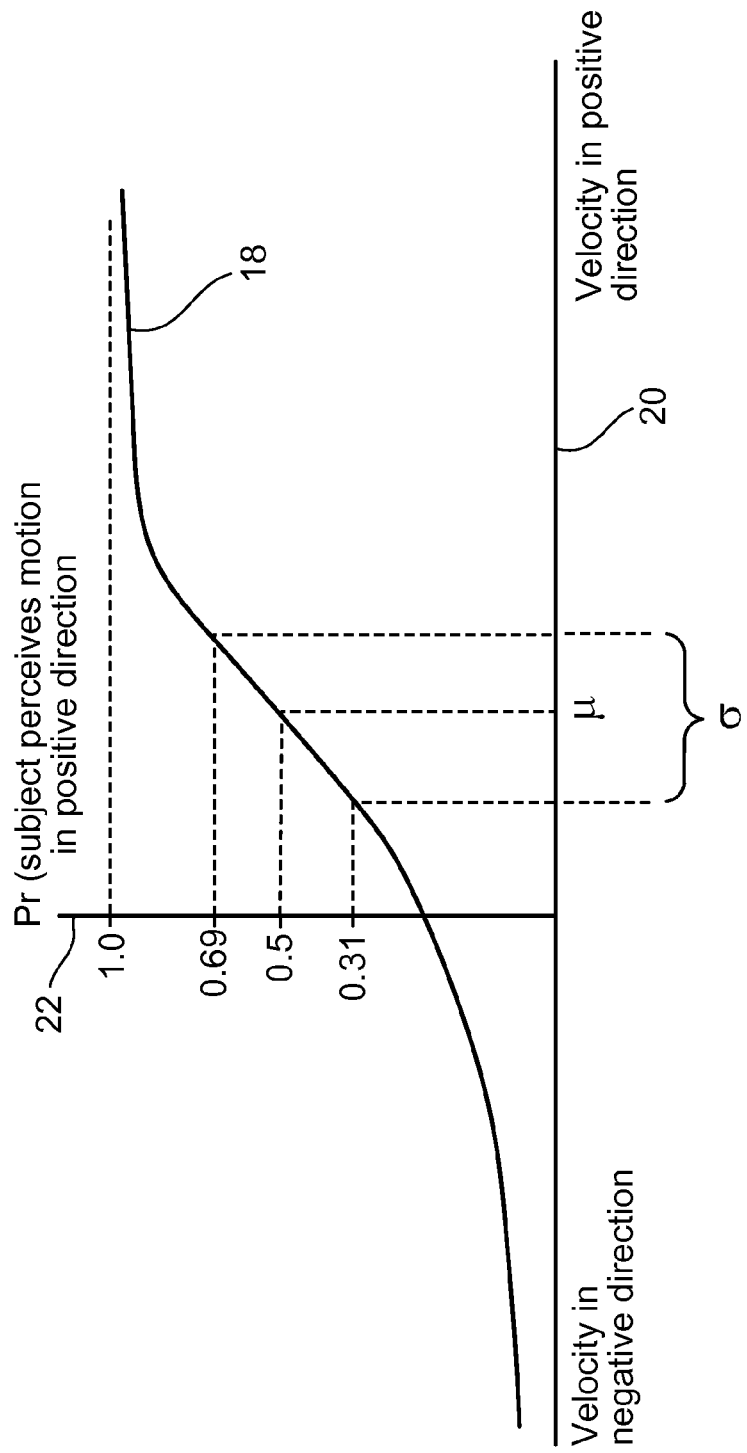
FIG. 2 is a graph that shows a psychometric function.

FIG. 2 shows a psychometric function 18 representing a probability that a subject will correctly perceive motion in a particular direction at a particular frequency. The horizontal axis 20 indicates the peak velocity of the motion profile experienced by a subject, with positive values indicating motion in one direction and negative values indicating motion in an opposite direction.

The vertical axis 22 indicates the estimated probability that, when subjected to motion in the positive or negative direction at a particular amplitude, a subject will perceive motion in the positive direction as a function of that motion's peak velocity amplitude. As is apparent, when the motion is in a positive direction at relatively high amplitude, the subject has no difficulty perceiving it. Hence, the probability of correctly perceiving the motion approaches 1.0. In contrast, when the motion is in the negative direction at high velocity, the subject rarely makes the mistake of perceiving motion in the positive direction. Thus, the probability that the subject will report positive motion given a high peak velocity in the negative direction would approach zero. At some amplitude in between, the probability that the subject correctly identifies positive motion reaches 50%, thus indicating that the subject can do no better than guessing. This amplitude, which is indicated on the horizontal axis as $\mu$, is a statistic that represents the vestibular "bias." Another statistic, the "threshold," or "spread," which is shown as $\sigma$ in FIG. 2, represents the slope of the psychometric function 18 in the vicinity of the vestibular threshold.

In some examples, the psychometric function is a parameterized Gaussian probability density function given by:

$$\Psi(x; b_1, b_2) = \frac{1}{2\pi} \int_{-\infty}^{b_1+b_2 x} \exp(-z^2/2) dz$$

For a series of responses by the subject, for example, at a single frequency, the procedure provides unbiased estimates of a parameter vector $[\hat{\mu}\ \hat{\sigma}]$ for the corresponding unbiased parameter vector $[\mu\ \sigma]$ of the psychometric function 18, or equivalently, estimates of the vector $[\hat{b}_1, \hat{b}_2]$ from which estimates of the parameter vector $[\mu\ \sigma]$ can be derived using the foregoing relationships. In either case, these estimates will have errors or uncertainties. It is these errors that are to be reduced by optimal selection of motions, thus reducing the time that a subject sits on the motion platform 12.

The estimation procedure generally includes assessing a subject's perception of motion for different kinds of motion. Typically, to estimate the statistics of the psychometric function 18, one causes the subject to experience a particular motion. Then, one records information indicative of the subject's perception of that motion. This information is then used to update the estimate of the statistics.

However, not all motions yield the same amount of useful data for estimating the shape of the psychometric function 18. Certain motions are information-poor. A subject's responses to these motions yield data that is of little or no help in estimating statistics of the psychometric function 18. Other motions are information-rich. A subject's responses to these motions yield data that greatly refines these same estimates. The estimation procedure described herein is intended to avoid information-poor motions and in favor of information-rich motions. The procedure does so by adaptively selecting subsequent motions based on estimates resulting from preceding motions. Providing information-rich motions helps reduce testing time, since fewer information-rich trials are required than for information-poor trials.

The subject can provide the responses in various ways. In some implementations, the subject can provide the responses through hardwired buttons 19a or 19b, or another response device provided as a part of the motion platform 12. In some implementations, the responses can be received via a wired or wireless handheld device such as a tablet computer or smartphone.

Reorientation Aids

In some implementations, an overall testing time for a subject can be reduced significantly by providing a reorientation aid between two consecutive motion stimuli. In some implementations, providing the reorientation aid can include turning on a light source for a predetermined time period (e.g. for two seconds or less) immediately after the subject provides a response to a motion stimulus. The subsequent motion stimulus can then be provided after the light is again turned off. In some implementations, the reorientation aid can include turning on a light source for a predetermined time period while the subject provides a response to a motion stimulus. In some implementations, the reorientation aid can be provided after a fixed number of stimuli, for example, after every two, three, or more stimuli.

In some implementations, the orientation aid can include a reference object that the subject can use to reorient himself or herself. For example, a head-stationary image or object can be made visible to the subject during the predetermined time period to aid reorientation. Such a stationary object can help extinguish after-effects of the previous motion stimulus before a subsequent stimulus is provided. Alternatively, an earth-stationary image or object might be used.

In an example operation while using reorientation aids, initially the light source and the display of any illuminated input device (e.g., a tablet computer) are switched off. A motion stimulus is then provided to the subject and the tablet computer is enabled immediately afterwards to allow the subject to input a response while still in total darkness. The response (which can be, for example, a binary response), can be sent over a wired or wireless connection from the tablet computer to the processor 16. The reference object (e.g. a picture) is then illuminated by a light source in the otherwise dark testing room to allow the subject to reorient himself or herself. The tablet computer could be configured to simultaneously illuminate and accept a secondary input (e.g. a response or a confidence rating related to the response) from the user. The light source and the tablet computer are switched off within a predetermined interval before the next motion stimulus is then provided. In some implementations, the next motion stimulus can be selected adaptively, as described below.

By providing the reorientation aids between motion stimuli (also referred to as trials), inter-trial intervals can be reduced from 5 seconds or more to about 3 seconds or less. In situations where several hundred trials are administered, this can result in significant savings in testing time. For example, a test employing the methods described herein and comprising 150 trials with 5 second inter-trial intervals can be completed in about 18 minutes. With inter-trial intervals of 3 seconds, the same test can be completed in about 13 minutes. With inter-trial interval of 1 second, the same test can be completed in about 8 minutes. The reorientation aids can be used in conjunction with a combination of one or more of the systems and techniques described in this document. For example, the reorientation aids can be provided in a vestibular testing system that implements a combination of the techniques described below.

Adaptive Stimuli Selection

Figure 3:
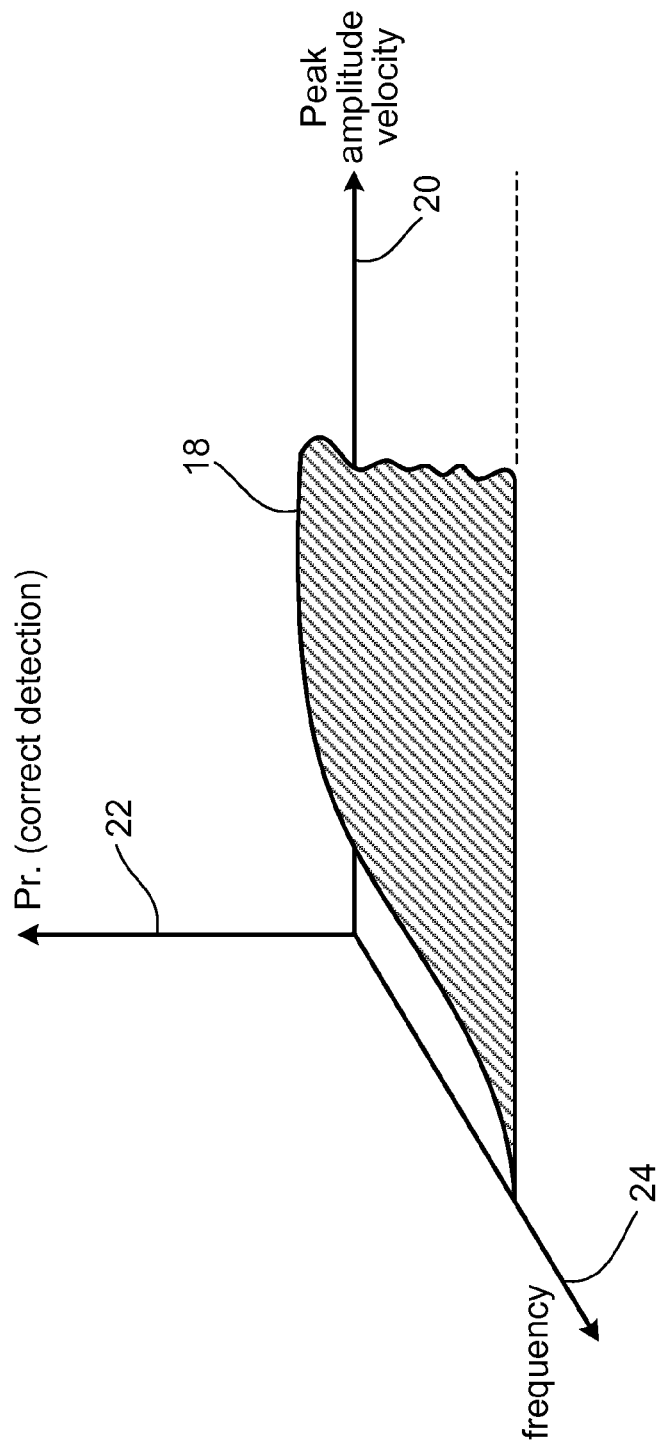
FIG. 3 is a graph that shows the psychometric function of FIG. 2 in a three-dimensional psychometric space.

One method for collecting threshold data includes defining a three-dimensional psychometric space having mutually orthogonal axes for frequency, velocity amplitude, and probability, as shown in FIG. 3. The plane defined by the velocity amplitude and frequency is the "stimulus plane." In this other approach, a psychometric function 18, such as that shown in FIG. 2, can be viewed as a slice through the three-dimensional psychometric space. For the psychometric function 18 shown in FIG. 2, that slice is a slice of constant frequency. A vestibulogram can be viewed as a curve connecting values of σ at different frequencies in the psychometric space shown in FIG. 3.

According to the foregoing method, the next point in the stimulus plane at which a measurement should be taken is that point that will provide the greatest additional information about the statistics of the psychometric function 18 given what is already known about those statistics. Equivalently, one chooses, as the next measurement point in the stimulus plane, that point for which a measurement would resolve uncertainty in the estimate to the greatest extent. The choice of the next point in the stimulus plane would then depend on what has already been learned about the subject's psychometric function 18. Consequently, this method can be viewed as an adaptive one.

In principle, the path through the stimulus plane is unconstrained. Thus, following measurement at one point (V1, f1) in the stimulus plane, the next measurement can be at (V2, f2) where V1≠V2 and/or f1≠f2. However, in many practical implementations, the next point following a measurement at (V1, f1) will be a point at (V2, f1).

Figure 4:
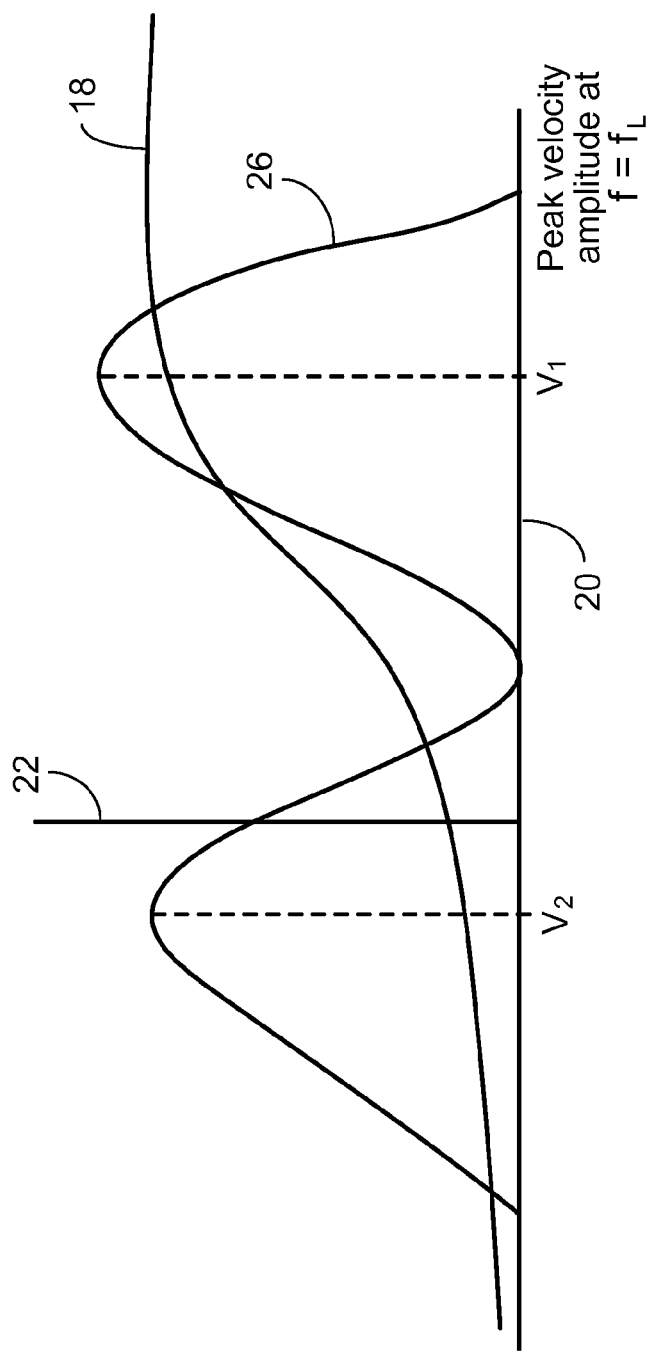
FIG. 4 is a graph that shows the psychometric function of FIG. 2 with Fisher information superimposed thereon.

One way to identify the next point in the stimulus plane at which to take a measurement is for the processor 16 to calculate the Fisher information 26 associated with a psychometric function 18, as shown in FIG. 4. The amplitude values at which the Fisher information has maxima would identify those amplitudes for which a measurement would provide the greatest resolution of ambiguity. For example, given the estimate of a psychometric function 18 in FIG. 4, the estimate would be best improved by determining the subject's response to motion at peak velocities of V1 and V2 at frequency f1 in the stimulus plane. The processor 16 would then instruct the controller 14 to cause the motion platform 12 to execute motions with those peak velocities. Based on the feedback provided by the user, the processor 16 then determines a new estimate of the psychometric function 18. These would yield a new estimate of the statistics of the psychometric function 18, with new Fisher information, which can then be used to identify one or more points in the stimulus plane for subsequent measurements.

In executing the foregoing method, both mean and spread of the psychometric function 18 are estimated. This differs from known methods of data acquisition for estimating perceptual threshold, in which the spread is assumed to be constant. This is of particular value when estimating a psychometric function 18 for a vestibular threshold because the spread itself can provide diagnostic information.

Figure 5:
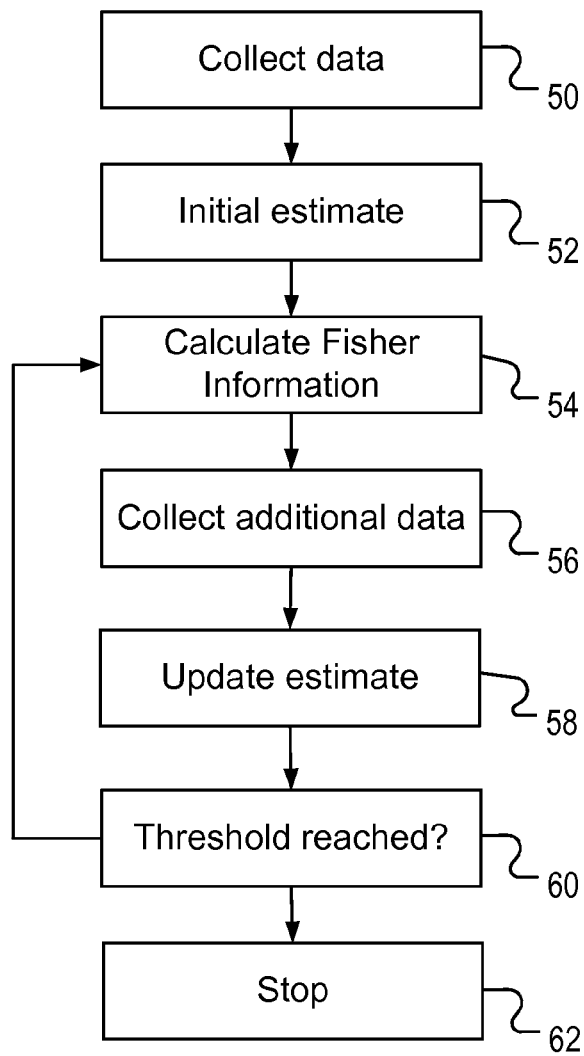
FIG. 5 is a flowchart showing execution of a data collection method.

Referring now to FIG. 5, a method for adaptively identifying points in the stimulus plane at which to collect data begins by collecting sufficient data (step 50) using a conventional method to derive an initial estimate of the statistics of a psychometric function (step 52). This can be carried out by using a conventional staircase method, such as a 2-down/1-up staircase. Once an initial estimate is provided, Fisher information for the estimate is calculated (step 54) and additional data is collected (step 56) at points in the stimulus plane identified by the Fisher information. The estimate of the psychometric function is then updated (step 58), preferably using a generalized linear model. This results in an updated estimate of various statistics associated with the psychometric function 18. If the updated estimate is deemed adequate, i.e. if some measure of goodness surpasses a pre-defined threshold (step 60), the procedure is terminated (step 62). Otherwise, the step of calculating Fisher information (step 54), this time based on the updated estimate, is carried out, followed by steps of collecting additional data at points in the stimulus plane based on the Fisher information (step 56) and updating the estimates yet again. The foregoing steps are typically carried out by the processor 16 in FIG. 1. In some implementations, for a staircase method, a parameter vector can be defined as [μ, σ] wherein μ equals zero and σ is a proportional to the staircase target percentage correct determined by the type of staircase. Various examples of staircase methods are described below in additional details.

Given a set of data points, each of which represents a subject's response to a stimulus defined by a point in the stimulus plane, an estimate of the parameter vector of the subject's psychometric function can be improved by executing certain steps to identify the best point in the stimulus plane at which to obtain the next response of the subject.

The procedure begins by obtaining a maximum likelihood estimate of the parameter vector given the existing responses collected from the subject. This estimate can optionally be corrected for measurement bias.

Next, one obtains an expression for the Fisher information, which is a function of a variable indicative of a point in the stimulus plane. This Fisher information will depend in part on the responses that have already been collected. As such, the Fisher information changes with each new measurement collected. The Fisher information represents, for each point in the stimulus plane, an extent to which the estimate of the parameter vector would be improved if a subject's response at that point were to be measured. For one point in the stimulus plane, the Fisher information, and hence the extent to which an estimate will be improved, can be maximized. The next step is to identify this point in the stimulus plane. Once this point is known, the subject is moved in accordance with the motion defined by that point, and his response to that motion collected. This iterative procedure can be repeated over again until a desired level of accuracy has been achieved.

In general, the point that maximizes the Fisher information can be anywhere in the stimulus plane. For example, the shape of the Fisher information may dictate that data be collected at a new motion frequency or a new motion amplitude from a preceding motion frequency or motion amplitude. In some practices, however, a constraint is imposed such that only amplitude may be varied and not frequency, or vice versa.

In some practices, the parameter vector consists of only vestibular bias and spread. However, in other practices, the parameter vector includes a frequency parameter indicative of the dependence of the vestibular bias on frequency and/or spread. The method described herein improves over the art in a number of ways. First, known methods make measurements at points in a pre-defined grid of points on the stimulus plane. This inevitably results in sub-optimal estimates, since the optimal points in the stimulus plane could not be known in advance. The method described herein avoids this disadvantage by adaptively making measurements at those points in the stimulus plane that are specifically optimized for maximizing the amount of information gleaned from each measurement.

Additionally, known methods of acquiring perception data typically attempt to estimate only one statistic, the mean, of the psychometric function 18, with the other, the spread, having an assumed value. This is inadequate in vestibular applications since the spread is a statistic of considerable interest. Moreover, since the Fisher information yields the optimal next measurement point in the stimulus plane based on an earlier estimate of both $\mu$ and $\sigma$, holding $\sigma$ fixed is likely to result in a less efficient data collection procedure, with efficiency being defined by the average amount of information yielded by each data collection event.

After having estimated statistics of a psychometric function by obtaining measurements at multiple points (V1, f1), (V2, f1) (Vn, f1), the next step is to proceed to a new frequency, f2. When moving to a new frequency, it is more efficient to begin testing with motion at a suitable amplitude for gathering data at that frequency.

One way to estimate a starting amplitude for a second frequency is to combine an estimate of both the vestibular threshold, $\mu$, and the spread, $\sigma$, at a first frequency f1 and previous knowledge concerning the overall frequency-dependence of $\mu$ and $\sigma$ to avoid selecting information-poor motions at a second frequency. For example, in the case of rotation, the dependence of vestibular threshold on frequency has been found to vary by a factor of (1+fc/f), where fc is a subject-dependent fit parameter that can viewed as a cutoff-frequency of a high pass filter. This relationship can be used to identify a suitable peak velocity for motion at a second frequency given an estimate at a first frequency and an estimate of a subject's high-pass filter cutoff frequency. This avoids wasting time using the motion platform 12 to execute information-poor motions.

One approach to reduce the time spent executing motions on the motion platform 12 is to attenuate the peak velocity of each trial at a new frequency f by a factor of (1+fc/f) and to perform a maximum likelihood estimate of fc on the data using a generalized linear model. This is equivalent to weighting the estimate by a high-pass filter transfer function having a subject-specific cutoff frequency, fc. The resulting maximum likelihood fit would yield a new estimate of fc together with improved estimates of $\mu$ and $\sigma$. Thus, at the end of each trial, there would be a revised estimate of $\mu$, $\sigma$ and fc. This process would proceed iteratively until the marginal improvements in the estimate, as represented by variance between successive estimates, are below a preselected threshold. Another approach is to numerically maximize the likelihood product (or equivalently, the log likelihood sum) over $\sigma$, $\mu$, and fc, where the likelihood product accumulated over N trials is:

$$\prod_{i=1}^{N} F(x_i, \alpha, \beta, k)^{Y_i}(1 - F(x_i, \alpha, \beta, k))^{1-Y_i}$$

$$\prod_{i=1}^{N} F(x_i, \alpha, \beta, k)^{Y_i}(1 - F(x_i, \alpha, \beta, k))^{1-Y_i}$$

where F is a cumulative distribution function, $\alpha$ and $\beta$ are two statistics of the distribution, such as mean and variance, k is a filter fit parameter, $x_i$ is a stimulus for the $i^{th}$ trial and $Y_i$ is 0 or 1 depending on the subject's response during the $i^{th}$ trial.

Yet another approach is to use Bayesian priors to represent prior knowledge of the shape of V(f) in either of the foregoing methods.

The use of generalized linear models to estimate statistics of the psychometric function 18 inherently provides a basis for correcting for any bias in the estimate of the mean of the psychometric function 18, even with a small number of data collection events. This is a particular advantage over conventional methods, which rely on the Nelder-Mead or similar optimization methods.

Despite the subject's best efforts at paying attention, the data collection process can be so grueling that there are inevitable lapses in the subject's concentration. These lapses manifest themselves in subject's responses that are completely inconsistent with that subject's previous responses to similar stimuli.

Known methods of correcting an estimate to accommodate lapses rely on assuming a continuous lapse rate. For example, in one known method, the probability of a correct response is modeled by $\psi(x; \alpha,\beta,\gamma,\lambda)=\gamma+(1-\gamma-\lambda)F(x; \alpha,\beta)$ where $F(x; \alpha,\beta)$ is a two-parameter cumulative probability density function, with $\gamma$ and $1-\lambda$ representing lower and upper bounds thereof, and $\lambda$ being interpreted as a lapse rate. This lapse rate, $\lambda$, is a continuous variable that represents a small fraction of trials for which a subject fails to provide a response. In conventional methods, the data-skewing effect of such outliers is mitigated by collecting more data.

A difficulty with the foregoing approach is that it tends to promote additional lapses. Typically, an attention lapse occurs because a subject, after having provided data for some time, simply becomes bored with the process. To ask such a subject, who may already be approaching the limits of his endurance, to provide even more data would appear to invite additional lapses, which would then introduce a need to generate still more lapses in a never-ending cycle.

An improvement in this known method is that of modeling a lapse as a discrete binary event, and instead applying objective statistical criteria to remove those lapses that are most influential in introducing an estimation error. Doing so reduces the overall number of fit parameters and enables one to use the generalized linear model, instead of a maximum likelihood model, to estimate the psychometric function 18.

A testing method as described herein substantially reduces data collection time required for assessing vestibular condition of a patient. In some cases, the reduction can be around 25%. However, in other cases the reduction can be as much as 50%. This reduction in data collection time is achieved by relying on Fisher information to collect data at values of amplitudes and frequencies for which the uncertainty in the estimate of the parameter vector will be most reduced. Thus, with each data collection event, the amount of information captured as a result of that event will tend to be monotonically decreasing on the average.

The methods and devices herein are described in operation in the context of a feedback loop in which subsequent motions are selected based on data collected from earlier motions. However, the methods and devices can also be used non-iteratively in connection with data to remove bias, to detect lapses, and to fit the psychometric function to data collected at multiple points on the stimulus plane, including points at different amplitudes but at the same frequency, or points at different frequencies. For example, one can fit a surface corresponding to the psychometric function to data points at various amplitudes and frequencies. In such cases, an estimation error to be minimized is minimized across all frequencies for which data points have been provided. Additional examples are described in the publication: Lim K., and Merfeld D. M., *Signal detection theory and vestibular perception: II. Fitting perceptual thresholds as a function of frequency*. Experimental Brain Research, 2012; 222 (3):303-20, the entire content of which is incorporated herein by reference.

In such cases, the sequence of motions carried out during data collection is not adaptively changed in response to results obtained during collection. However, the methods are then applied to the collected data to obtain more accurate estimates of the shape of the psychometric function. Since more information can then be extracted from each data point, fewer points would have to be collected to obtain an estimate of a particular veracity. Hence, the data collection procedure can be made significantly shorter, perhaps as much as 50% shorter.

Bias Reduction in Estimated Parameters

Psychometric tests can include estimating a subject's ability to perform a specific task as a function of a stimulus. The subject's responses are collected as a data set corresponding to a test parameter associated with the provided stimuli. In some implementations, the test parameter for a given dataset can be a reciprocal of the time duration for which each stimulus is provided. This test parameter is often referred to as frequency. In some implementations, one or more functions are fitted on the dataset(s) acquired through a psychometric test and one or more parameters for the fitted functions are estimated. The fitted functions are often referred to as psychometric functions.

In fitting psychometric functions to datasets acquired using, for example, adaptive sampling procedures (e.g., "staircase" procedures), a bias in the fit parameters is often encountered. In some implementations, the bias can be attributed to the serial dependency of the adaptive data. In some implementations, for cumulative Gaussian parametric maximum likelihood fits on data collected via adaptive sampling procedures, a bias-reduced maximum likelihood fit can be used to substantially reduce the bias without reducing the precision of the fit parameter estimate and without reducing the accuracy or precision of other fit parameters. The bias-reduction technique can be implemented using, for example, generalized linear model fits or other numeric maximum likelihood techniques such as the Nelder-Mead simplex. In some implementations, bias-reduced maximum likelihood fits can be applied to forced choice, binary, psychometric data collected using adaptive sampling procedures. The fit parameters can be estimated using a small number of trials (e.g. less than 200, or in some cases, less than 50) for a given level of accuracy and precision. This is advantageous in various applications, such as vestibular testing where presenting motion stimuli is time consuming. In some implementations, parameter bias can be corrected by eliminating a first order asymptotic parameter bias that typically diminishes with $1/n$, n being the number of trials.

In some implementations, the parameter bias can be reduced by calculating the expected percent size of the bias in advance and removing the bias by multiplying the biased estimate by a scale factor. However, when the estimate is downwardly biased, as for the spread parameter ($\sigma$) in some cases, the scale factor is greater than one. This causes the variance on the estimated parameter to increase. Alternatively, when an estimated parameter is upwardly biased, the scale factor is less than one, which reduces both the bias and the variance of the estimate. By forcing an estimated parameter to be upwardly biased and using a scale factor in combination with bias-reduced maximum likelihood estimation, can improve both the accuracy and precision of the estimated parameters for very small data sets (e.g. 25 trials or lower).

As an alternative, provided below are equations that allow a reduction in the downward bias on the estimated $\sigma$ (referred to as $\hat{\sigma}$) without significantly increasing the variance on $\hat{\sigma}$ or the estimated mean $\hat{\mu}$, and without decreasing the accuracy on $\hat{\mu}$. The biased-reduced maximum likelihood estimation can also improve the symmetry of the distribution for small number of trials.

Bias-Reduced Generalized Linear Model (GLM)

To implement the bias-reduced generalized linear model (BRGLM) routine, a generalized linear model fit (e.g., as available in a MATLAB function glmfit.m) can be modified such that during each iteration of the GLM reweighted least squares algorithm, the order $n^{-1}$ asymptotic bias term is calculated and subtracted from our coefficient parameter estimate, $\hat{b}$. The order $n^{-1}$ asymptotic bias term is calculated using the following formula $$(X^T W X)^{-1} X^T W \xi$$

$$(X^T W X)^{-1} X^T W \xi$$

where n is the number of trials, X is the stimulus vector (with a first column of ones if the constant $b_1$ term is to be included in the model) and W is the quadratic weights vector (diagonalized into a matrix) which is inversely related to the variance of the subject's binary responses. For non-canonical models such as a probit link, the components of $\xi$ are given by:

$$\xi_i = -\frac{1}{2}\left(\frac{u_i''}{u_i'}\right) Q_{ii}$$

$$\xi_i = -\frac{1}{2}\left(\frac{u_i''}{u_i'}\right) Q_{ii}$$

where $u'_i = \partial u_i / \partial m_i, u'_i = \partial u_i / \partial m_i$ and $u''_i = \partial^2 u_i / \partial m_i^2, u''_i = \partial^2 u_i / \partial m_i^2$ are the derivative of the GLM link function ($u_i$), and $$m_i = \hat{b}_1 + \hat{b}_2 x_i$$

and $$Q = X(X^T W X)^{-1} X^T.$$

For the probit model, the link function is the cumulative standard Gaussian distribution $$[u_i = \psi_i = \phi(m_i) = \phi(\hat{b}_1 + \hat{b}_2 x_i)],$$

and therefore $$\xi_i = Q_i n_i / 2$$

Bias-Reduction in Numeric Maximum Likelihood Fits

In some implementations, bias-reduced psychometric function parameter estimates can also be determined for numeric maximum likelihood fits. In some implementations, bias-reduction techniques can help reduce testing time, since bias reduction techniques require fewer trials to yield substantially the same accuracy as techniques without bias reduction and because bias-reduced parameters allow for targeting more information-rich stimulus levels as described in detail earlier. The bias-reduction can also be implemented in the presence of a lapse rate or nonlinear asymmetry. To implement bias reduction in constrained numeric maximum likelihood fits the bias vector can be calculated by modifying the score function (U), which can be the gradient of a log-likelihood function. In the present example, the log-likelihood function for the binary response model is given by:

$$l(b_1, b_2; x, y) = \sum_{i=1}^{n} [\log(y_i \psi(x_i; b_1, b_2) + (1 - y_i)(1 - \psi(x_i; b_1, b_2)))]$$

$$l(b_1, b_2; x, y) = \sum_{i=1}^{n} [\log(y_i \psi(x_i; b_1, b_2) + (1 - y_i)(1 - \psi(x_i; b_1, b_2)))]$$

where x is the stimulus vector and y is the binary response vector. In some implementations, a lapse rate γ can also be included by modifying as $\psi$ as $\psi(x_i; b_1, b_2, \gamma)$. In some implementations, where a nonlinear asymmetry is included, the equation for the modified asymmetric psychometric function replaces $\psi$ in the above equation.

The maximum likelihood estimate can be the solution to the equation $U = \Delta l = 0$. Similarly, the bias-reduced maximum likelihood estimate is the solution $U + A = 0$ where A is a correction function based either on the expected or observed information matrix. Using summation notation, A can be defined as:

$$A_r = K^{u,v}(K_{r,u,v} + K_{r,uv})/2$$

$$A_r = K^{u,v}(K_{r,u,v} + K_{r,uv})/2$$

where $K^{u,v}$ denotes the inverse of the expected information matrix $$K_{r,u,v} = n^- E[U_r U_u U_v] K_{r,u,v} = n^{-1} E[U_r U_u U_v]$$

and $$K_{r,uv} = n^{-1} E[U_r U_{uv}].$$

$$K_{r,uv} = n^{-1} E[U_r U_{uv}].$$

Considering the probit model in the (b1, b2) parameterization and letting $$c_i = (2y_i - 1)/(y_i \psi_i + (1 - y_i)(1 - \psi_i))$$

$$c_i = (2y_i - 1)/(y_i \psi_i + (1 - y_i)(1 - \psi_i)),$$

the score vector is determined to have the following components:

$$U_{b_1} = \sum_{i=1}^{n} c_i \frac{\partial \psi_i}{\partial b_1},$$

$$U_{b_2} = \sum_{i=1}^{n} c_i \frac{\partial \psi_i}{\partial b_2}$$

$$U_{b_1} = \sum_{i=1}^{n} c_i \frac{\partial \psi_i}{\partial b_1},$$

$$U_{b_2} = \sum_{i=1}^{n} c_i \frac{\partial \psi_i}{\partial b_2},$$

which yields the observed information matrix to be:

$$i = -\begin{bmatrix} \sum_{i=1}^{n} c_i \frac{\partial^2 \psi_i}{\partial b_1^2} - \left(c_i \frac{\partial \psi_i}{\partial b_1}\right)^2 & \sum_{i=1}^{n} c_i \frac{\partial^2 \psi_i}{\partial b_1 \partial b_2} - (c_i)^2 \frac{\partial \psi_i}{\partial b_1} \frac{\partial \psi_i}{\partial b_2} \\ \sum_{i=1}^{n} c_i \frac{\partial^2 \psi_i}{\partial b_1 \partial b_2} - (c_i)^2 \frac{\partial \psi_i}{\partial b_1} \frac{\partial \psi_i}{\partial b_2} & \sum_{i=1}^{n} c_i \frac{\partial^2 \psi_i}{\partial b_2^2} - \left(c_i \frac{\partial \psi_i}{\partial b_2}\right)^2 \end{bmatrix}$$

$$i = -\begin{bmatrix} \sum_{i=1}^{n} c_i \frac{\partial^2 \psi_i}{\partial b_1^2} - \left(c_i \frac{\partial \psi_i}{\partial b_1}\right)^2 & \sum_{i=1}^{n} c_i \frac{\partial^2 \psi_i}{\partial b_1 \partial b_2} - (c_i)^2 \frac{\partial \psi_i}{\partial b_1} \frac{\partial \psi_i}{\partial b_2} \\ \sum_{i=1}^{n} c_i \frac{\partial^2 \psi_i}{\partial b_1 \partial b_2} - (c_i)^2 \frac{\partial \psi_i}{\partial b_1} \frac{\partial \psi_i}{\partial b_2} & \sum_{i=1}^{n} c_i \frac{\partial^2 \psi_i}{\partial b_2^2} - \left(c_i \frac{\partial \psi_i}{\partial b_2}\right)^2 \end{bmatrix}$$

Under the assumption $$g_i = (\psi_i(1 - \psi_i))^{-1}$$

$$g_i = (\psi_i(1 - \psi_i))^{-1}$$

the expected information matrix becomes:

$$I = E[i] = \begin{bmatrix} \sum_{i=1}^{n} \left(\frac{\partial \psi_i}{\partial b_1}\right)^2 g_i & \sum_{i=1}^{n} \left(\frac{\partial \psi_i}{\partial b_1}\right)\left(\frac{\partial \psi_i}{\partial b_2}\right) g_i \\ \sum_{i=1}^{n} \left(\frac{\partial \psi_i}{\partial b_1}\right)\left(\frac{\partial \psi_i}{\partial b_2}\right) g_i & \sum_{i=1}^{n} \left(\frac{\partial \psi_i}{\partial b_2}\right)^2 g_i \end{bmatrix}$$

$$I = E[i] = \begin{bmatrix} \sum_{i=1}^{n} \left(\frac{\partial \psi_i}{\partial b_1}\right)^2 g_i & \sum_{i=1}^{n} \left(\frac{\partial \psi_i}{\partial b_1}\right)\left(\frac{\partial \psi_i}{\partial b_2}\right) g_i \\ \sum_{i=1}^{n} \left(\frac{\partial \psi_i}{\partial b_1}\right)\left(\frac{\partial \psi_i}{\partial b_2}\right) g_i & \sum_{i=1}^{n} \left(\frac{\partial \psi_i}{\partial b_2}\right)^2 g_i \end{bmatrix}$$

The remaining quantities required to calculate A can be found below. Once those have been calculated we can then use numeric methods to solve $U + A = 0$ to find the bias-reduced maximum likelihood estimates. Under the following conditions:

$$h_i = (\psi_i)^{-2} - (1 - \psi_i)^{-2}$$

$$h_i = (\psi_i)^{-2} - (1 - \psi_i)^{-2}$$

the remaining quantities required to calculate A are as follows:

$$K_{b_1,b_1,b_1} = \frac{1}{n}\sum_{i=1}^{n}\left(\frac{\partial \psi_i}{\partial b_1}\right)^3 h_i$$

$$K_{b_1,b_1,b_2} = \frac{1}{n}\sum_{i=1}^{n}\left(\frac{\partial \psi_i}{\partial b_1}\right)^2\left(\frac{\partial \psi_i}{\partial b_2}\right) h_i$$

$$K_{b_1,b_2,b_2} = \frac{1}{n}\sum_{i=1}^{n}\left(\frac{\partial \psi_i}{\partial b_1}\right)^2\left(\frac{\partial \psi_i}{\partial b_2}\right)^2 h_i$$

$$K_{b_2,b_2,b_2} = \frac{1}{n}\sum_{i=1}^{n}\left(\frac{\partial \psi_i}{\partial b_2}\right)^3 h_i$$

$$K_{b_1,b_1,b_1} = \frac{1}{n}\sum_{i=1}^{n}\left[\left(\frac{\partial \psi_i}{\partial b_1}\right)\left(\frac{\partial^2 \psi_i}{\partial b_1^2}\right)g_i - \left(\frac{\partial \psi_i}{\partial b_1}\right)^3 h_i\right]$$

$$K_{b_1,b_1,b_2} = \frac{1}{n}\sum_{i=1}^{n}\left[\left(\frac{\partial \psi_i}{\partial b_1}\right)\left(\frac{\partial^2 \psi_i}{\partial b_1 \partial b_2}\right)g_i - \left(\frac{\partial \psi_i}{\partial b_1}\right)^2\left(\frac{\partial \psi_i}{\partial b_2}\right) h_i\right]$$

$$K_{b_1,b_2,b_2} = \frac{1}{n}\sum_{i=1}^{n}\left[\left(\frac{\partial \psi_i}{\partial b_1}\right)\left(\frac{\partial^2 \psi_i}{\partial b_2^2}\right)g_i - \left(\frac{\partial \psi_i}{\partial b_1}\right)\left(\frac{\partial \psi_i}{\partial b_2}\right)^2 h_i\right]$$

$$K_{b_2,b_1,b_1} = \frac{1}{n}\sum_{i=1}^{n}\left[\left(\frac{\partial^2 \psi_i}{\partial b_1^2}\right)\left(\frac{\partial \psi_i}{\partial b_2}\right)g_i - \left(\frac{\partial \psi_i}{\partial b_1}\right)^2\left(\frac{\partial \psi_i}{\partial b_2}\right) h_i\right]$$

$$K_{b_2,b_1,b_2} = \frac{1}{n}\sum_{i=1}^{n}\left[\left(\frac{\partial \psi_i}{\partial b_2}\right)\left(\frac{\partial^2 \psi_i}{\partial b_1 \partial b_2}\right)g_i - \left(\frac{\partial \psi_i}{\partial b_1}\right)\left(\frac{\partial \psi_i}{\partial b_2}\right)^2 h_i\right]$$

$$K_{b_2,b_2,b_2} = \frac{1}{n}\sum_{i=1}^{n}\left[\left(\frac{\partial \psi_i}{\partial b_2}\right)\left(\frac{\partial^2 \psi_i}{\partial b_2^2}\right)g_i - \left(\frac{\partial \psi_i}{\partial b_2}\right)^3 h_i\right]$$

$$K_{b_1,b_1,b_1} = \frac{1}{n}\sum_{i=1}^{n}\left(\frac{\partial \psi_i}{\partial b_1}\right)^3 h_i$$

$$K_{b_1,b_1,b_2} = \frac{1}{n}\sum_{i=1}^{n}\left(\frac{\partial \psi_i}{\partial b_1}\right)^2\left(\frac{\partial \psi_i}{\partial b_2}\right) h_i$$

$$K_{b_1,b_2,b_2} = \frac{1}{n}\sum_{i=1}^{n}\left(\frac{\partial \psi_i}{\partial b_1}\right)\left(\frac{\partial \psi_i}{\partial b_2}\right)^2 h_i$$

$$K_{b_2,b_2,b_2} = \frac{1}{n}\sum_{i=1}^{n}\left(\frac{\partial \psi_i}{\partial b_2}\right)^3 h_i$$

$$K_{b_1,b_1,b_1} = \frac{1}{n}\sum_{i=1}^{n}\left[\left(\frac{\partial \psi_i}{\partial b_1}\right)\left(\frac{\partial^2 \psi_i}{\partial b_1^2}\right)g_i - \left(\frac{\partial \psi_i}{\partial b_1}\right)^3 h_i\right]$$

$$K_{b_1,b_1,b_2} = \frac{1}{n}\sum_{i=1}^{n}\left[\left(\frac{\partial \psi_i}{\partial b_1}\right)\left(\frac{\partial^2 \psi_i}{\partial b_1 \partial b_2}\right)g_i - \left(\frac{\partial \psi_i}{\partial b_1}\right)^2\left(\frac{\partial \psi_i}{\partial b_2}\right) h_i\right]$$

$$K_{b_1,b_2,b_2} = \frac{1}{n}\sum_{i=1}^{n}\left[\left(\frac{\partial \psi_i}{\partial b_1}\right)\left(\frac{\partial^2 \psi_i}{\partial b_2^2}\right)g_i - \left(\frac{\partial \psi_i}{\partial b_1}\right)\left(\frac{\partial \psi_i}{\partial b_2}\right)^2 h_i\right]$$

$$K_{b_2,b_1,b_1} = \frac{1}{n}\sum_{i=1}^{n}\left[\left(\frac{\partial^2 \psi_i}{\partial b_1^2}\right)\left(\frac{\partial \psi_i}{\partial b_2}\right)g_i - \left(\frac{\partial \psi_i}{\partial b_1}\right)^2\left(\frac{\partial \psi_i}{\partial b_2}\right) h_i\right]$$

$$K_{b_2,b_1,b_2} = \frac{1}{n}\sum_{i=1}^{n}\left[\left(\frac{\partial \psi_i}{\partial b_2}\right)\left(\frac{\partial^2 \psi_i}{\partial b_1 \partial b_2}\right)g_i - \left(\frac{\partial \psi_i}{\partial b_1}\right)\left(\frac{\partial \psi_i}{\partial b_2}\right)^2 h_i\right]$$

$$K_{b_2,b_2,b_2} = \frac{1}{n}\sum_{i=1}^{n}\left[\left(\frac{\partial \psi_i}{\partial b_2}\right)\left(\frac{\partial^2 \psi_i}{\partial b_2^2}\right)g_i - \left(\frac{\partial \psi_i}{\partial b_2}\right)^3 h_i\right]$$

Additional examples related to the bias reduction techniques described above can be found in the publication: Chaudhuri S. E., and Merfeld D. M., *Signal detection theory and vestibular perception: III. Estimating unbiased fit parameters for psychometric functions,* Experimental Brain Research, 2013; 225(1):133-46.

Figure 6:
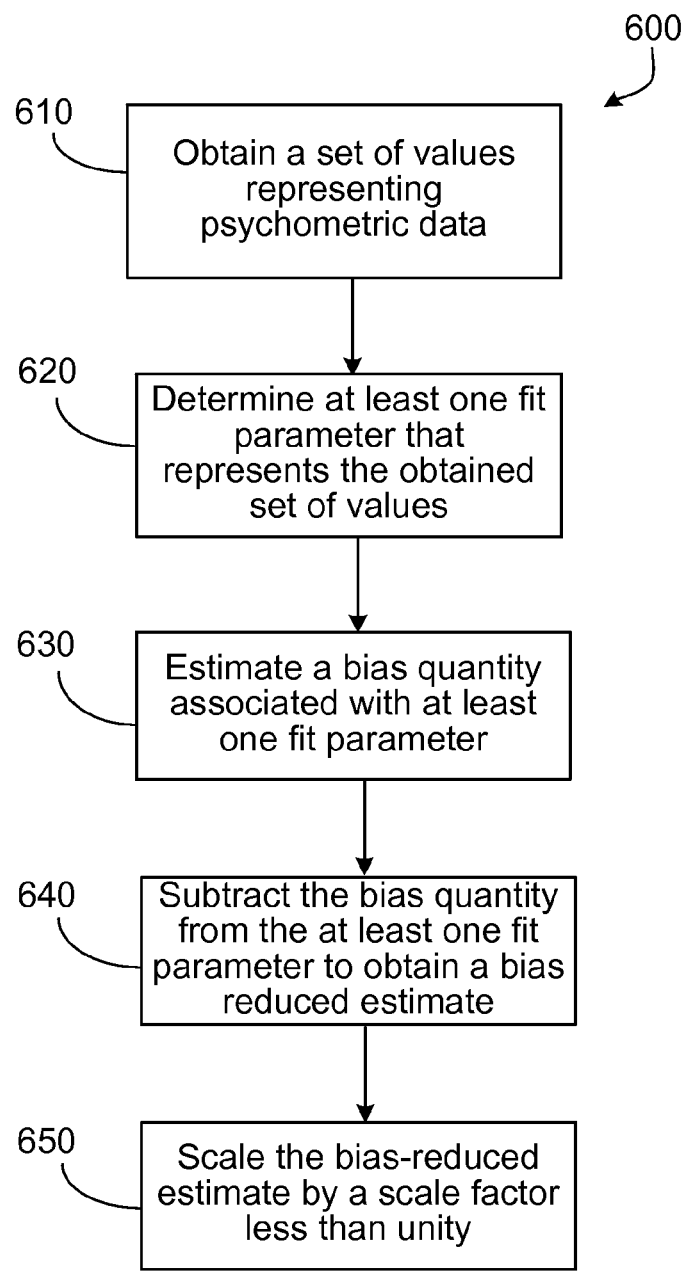
FIG. 6 is flowchart showing an example of a sequence of operations for reducing a bias in an estimated parameter.

FIG. 6 shows a flowchart 600 depicting an example of a sequence of operations for reducing a bias in an estimated parameter. The operations can be performed by a processor such as the processor 16 described with reference to FIG. 1. Operations can include obtaining a set of values representing psychometric data (610). For example, the set of values can include vestibular test data obtained using the data collection system described with reference to FIG. 1. In some implementations the set of data include test data for measuring a threshold that varies as a function of some parameter (or parameters) in a way that can be quantified and modeled. For example, the set of data can include perimetry test data for estimating visual thresholds that vary as a function of, for example, retinal location or frequency of light. The set of data can be obtained, for example, by administering a psychometric test to a subject and measuring responses of the subject. The responses of the subject can be measured, for example, for stimuli corresponding to a plurality of values of a test parameter. In some implementations, the responses to different values of the test parameter can be scaled using a corresponding scaling function to obtain the set of values that represent the psychometric data. The psychometric test can include, for example, providing a stimulus to the subject and the test parameter can be a reciprocal of a time duration for which the stimulus is provided. In some implementations, the psychometric test can include an adaptive sampling procedure. The psychometric test can include, for example, providing a stimulus for a predetermined number of times (e.g., 200 times or less, 100 times or less, 50 times or less) and measure the responses of the subject to obtain the set of data.

In some implementations, administering the psychometric test can include, for example, positioning the subject on a motion platform (e.g. the motion platform 12 described with reference to FIG. 1) configured to execute motion profiles, and obtaining an estimate of a parameter vector of the subject's psychometric function based on information indicative of the subject's perception of motion in response to a motion profile set. A subsequent motion profile can then be selected based on the estimate.

Operations can also include determining at least one fit parameter that represents the obtained set of data values (620). The fit parameter can be determined, for example, using cumulative Gaussian parametric maximum likelihood fits on data collected via adaptive sampling procedures. In some implementations, the fit parameter can be determined using a generalized linear model (GLM). In some implementations, the fit parameter can be determined using a numerical maximum-likelihood method.

Operations also include estimating a bias quantity associated with at least one of the fit parameters (630). In some implementations, the bias quantity can be estimated as an expected percent size of the bias. When GLM is used, the bias can be estimated as an asymptotic bias term during each iteration of the GLM reweighted least squares algorithm. Operations also include subtracting the bias quantity from the at least one fit parameter to obtain a bias reduced estimate (640).

In some implementations, operations 620, 630 and 640 can be repeated until a termination criterion is met. For example, two or more iterations of these operations can be conducted until a sufficiently bias reduced estimate is determined.

Operations can also include scaling the bias-reduced estimate by a scale factor less than unity (650), which is determined via numerical simulations of the experimental procedure being utilized. The subtraction of the bias quantity, determined using the provided equations, prior to scaling can reduce the bias and force the estimate to be upward-biased and therefore the scale factor is less than unity. Scaling by a scale factor less than unity reduces both the bias and the variance of the estimate.

Results

The parameter bias was substantially reduced using bias-reduced maximum likelihood estimation. These corrections worked on various adaptive sampling procedures without increasing the variance on $\hat{\mu}$ and $\hat{\sigma}$ or decreasing the accuracy of $\hat{\mu}$. In the case of a small number of trials (n=50) and the presence of a vestibular bias ($\mu=0.5\sigma$), bias-reduced maximum likelihood estimation reduced the bias, variance and skewness of the parameter estimates. Furthermore, bias-reduction substantially improved $\hat{\sigma}$ estimates for a staircase procedure with very small n (e.g., 25 trials), and these bias-reduced estimates were further improved by utilizing a pre-determined scale factor.

In some implementation, bias reduction allows for a direct comparison of data sets having different numbers of trials. Typically the amount or level of bias decreases as the number of trials increases. The technique described here allows for a direct comparison of data for different subjects even when the number of trials is different for the subjects. Bias reduction also allows for comparing datasets obtained using different staircase procedures—for example comparing data obtained using 3D/1U and 4D/1U staircases. Bias reduction also allows for comparing thresholds obtained using staircase procedures to those obtained via any other procedure (e.g., non-adaptive methods). For example, in the clinic, an unbiased estimate obtained using a bias-reduction technique can be compared to an unbiased normative data set obtained using a different methodology. For example, consider that a normative data set (with $\mu=0$) was obtained using an Maximum Likelihood Estimation (MLE) procedure with n=200, while a patient's data set (also with $\mu=0$) was obtained using a staircase procedure with n=50. If the patient had a normal threshold, and GLM fits were used to fit both the patient and the normative data, then the patient's threshold would be, on average, 6% lower than the normative average as shown in Table 1 below. On the other hand, if bias-reduced fits described here were used to fit both the patient and normative data, then the patient's threshold would only be, on average, 1% higher than the normative average (Table 1).

TABLE 1

Table 1: GLM and BRGLM $\hat{\mu}$ and $\hat{\sigma}$ means ± (standard deviations) for all simulations

| $\mu$ | # of Trials | Procedure | GLM: $\hat{\mu}$ | BRGLM: $\hat{\mu}$ | GLM: $\hat{\sigma}$ | BRGLM: $\hat{\sigma}$ |
|---|---|---|---|---|---|---|
| $\mu = 0$ | n = 50 | 3D/1U | 0.00 ± (0.24) | 0.00 ± (0.23) | 0.93 ± (0.26) | 1.01 ± (0.27) |
| | | 4D/1U | 0.01 ± (0.30) | 0.01 ± (0.25) | 0.91 ± (0.26) | 1.02 ± (0.25) |
| | | MLE | 0.00 ± (0.24) | 0.00 ± (0.24) | 0.93 ± (0.24) | 1.00 ± (0.26) |
| | | Non-Adaptive | 0.00 ± (0.22) | 0.00 ± (0.21) | 1.00 ± (0.27) | 1.06 ± (0.27) |
| | n = 100 | 3D/1U | 0.00 ± (0.15) | 0.00 ± (0.15) | 0.97 ± (0.17) | 1.00 ± (0.18) |
| | | 4D/1U | 0.00 ± (0.17) | 0.00 ± (0.17) | 0.97 ± (0.16) | 1.00 ± (0.16) |
| | | MLE | 0.00 ± (0.17) | 0.00 ± (0.17) | 0.97 ± (0.15) | 1.00 ± (0.16) |
| | | Non-Adaptive | 0.00 ± (0.15) | 0.00 ± (0.15) | 1.00 ± (0.18) | 1.03 ± (0.18) |
| | n = 200 | 3D/1U | 0.00 ± (0.10) | 0.00 ± (0.10) | 0.98 ± (0.12) | 1.00 ± (0.12) |
| | | 4D/1U | 0.00 ± (0.11) | 0.00 ± (0.11) | 0.99 ± (0.11) | 1.00 ± (0.11) |
| | | MLE | 0.00 ± (0.12) | 0.00 ± (0.12) | 0.99 ± (0.10) | 1.00 ± (0.10) |
| | | Non-Adaptive | 0.00 ± (0.10) | 0.00 ± (0.10) | 1.00 ± (0.12) | 1.01 ± (0.12) |
| $\mu = 0.5\sigma$ | n = 50 | 3D/1U | 0.53 ± (0.29) | 0.49 ± (0.24) | 0.86 ± (0.33) | 1.02 ± (0.27) |
| | | 4D/1U | 0.59 ± (3729) | 0.48 ± (0.26) | 0.80 ± (0.37) | 1.05 ± (0.26) |
| | | MLE | 0.49 ± (0.25) | 0.49 ± (0.24) | 0.91 ± (0.27) | 0.99 ± (0.28) |
| | | Non-Adaptive | 0.52 ± (0.24) | 0.49 ± (0.24) | 0.99 ± (0.30) | 1.07 ± (0.29) |
| | n = 100 | 3D/1U | 0.50 ± (0.17) | 0.49 ± (0.16) | 0.95 ± (0.19) | 1.00 ± (0.18) |
| | | 4D/1U | 0.52 ± (0.37) | 0.50 ± (0.18) | 0.94 ± (0.21) | 1.01 ± (0.17) |
| | | MLE | 0.50 ± (0.17) | 0.50 ± (0.17) | 0.97 ± (0.16) | 1.00 ± (0.16) |
| | | Non-Adaptive | 0.51 ± (0.16) | 0.51 ± (0.16) | 1.00 ± (0.19) | 1.03 ± (0.19) |
| | n = 200 | 3D/1U | 0.50 ± (0.11) | 0.50 ± (0.11) | 0.98 ± (0.12) | 1.00 ± (0.12) |
| | | 4D/1U | 0.50 ± (0.12) | 0.50 ± (0.12) | 0.98 ± (0.12) | 1.01 ± (0.12) |
| | | MLE | 0.50 ± (0.12) | 0.50 ± (0.12) | 0.99 ± (0.10) | 1.00 ± (0.10) |
| | | Non-Adaptive | 0.50 ± (0.11) | 0.50 ± (0.11) | 1.00 ± (0.13) | 1.02 ± (0.13) |

Category 1 Bias (<10% of stdev) Category II Bias (10-25% of stdev) Category III Bias (>25% of stdev)

Obtaining a Unified Dataset from Multiple Datasets

In some implementations, a bias-reduced parameter estimate can be computed based on a unified dataset obtained from a plurality of datasets corresponding to different parameters. For example, data sets obtained for different test parameters in a psychometric test can be mapped on to the unified dataset. In some implementations, the test parameter is frequency, i.e., a reciprocal of the duration of time for which a stimulus is provided in a given trial of a psychometric test. In some implementations, fit parameters can be estimated, for example, by performing psychometric fits at each frequency to obtain the fit parameters as functions of frequencies and then fitting a model to find a representative fit parameter. Fit parameters can also be estimated based on a unified dataset. The unified dataset can be obtained, for example, by computing a scaling function that scales the motion stimulus amplitude vector for a given frequency to fit a single psychometric function. The unified dataset therefore includes scaled data points from various frequencies. The scaling functions for the various frequencies can be characterized by corresponding sets of one or more scaling parameters.

In some implementations, estimating fit parameters based on the unified dataset can be more accurate, more precise, more robust, and more efficient than estimating the fit parameters at each frequency individually and then determining a representative fit parameter from the various estimated fit parameters. To estimate the fit parameters at each frequency individually, the number of trials at each frequency must be large enough to ensure adequate accuracy and precision. Fitting a maximum likelihood fit for each frequency with a small number of trials can yield threshold underestimation due to the small number of available data points.

In some implementations, stimulus vectors across all frequencies can be scaled (using appropriate scaling functions) to a unified dataset before fitting a single dimensionless psychometric function to the unified dataset. This is based on recognizing that if the brain is attenuating (e.g., filtering) a signal, then other signals can be attenuated (or scaled) by the same amount to yield the magnitude of neural signal being discriminated. Upon such scaling, a single psychometric function can be fitted to the scaled individual trial data (in the unified dataset) simultaneously across all frequencies, yielding the representative fit parameters. For the unified dataset, the values on the x-axis of the psychometric function no longer correspond to actual stimulus magnitude, but instead represent theoretical magnitude of the neural signal. Therefore the fit parameters based on the unified dataset correspond to a given magnitude of the neural signal regardless of frequency.

Additional examples of obtaining the unified dataset are illustrated in the publication: Lim K., and Merfeld D. M., *Signal detection theory and vestibular perception: II. Fitting perceptual thresholds as a function of frequency.* Experimental Brain Research, 2012; 222(3):303-20, the entire content of which is incorporated herein by reference. In some implementations, using a unified dataset to determine the fit parameters potentially alleviates the under-estimation problem because the number of data points used to determine the fit parameters is typically greater than the average number of trials at each frequency.

Figure 7A:
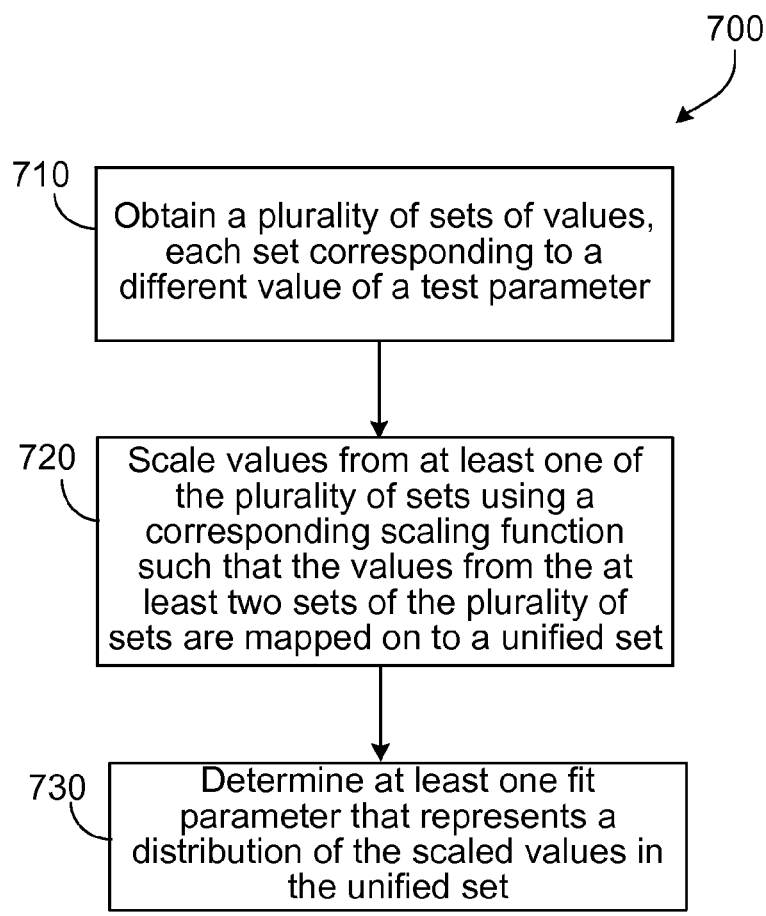
FIG. 7A is a flowchart showing an example of a sequence of operations for estimating a fit parameter.

FIG. 7A is a flowchart 700 showing an example of a sequence of operations for estimating a fit parameter. The operations can be performed by a processor such as the processor 16 described with reference to FIG. 1. Operations can include obtaining a plurality of sets of values, each set corresponding to a different value of a test parameter (710). Each value in the sets of values can be included in a set of discrete values. In some implementations, a psychometric test can be administered to a subject and responses of the subject can be measured to obtain the plurality of sets of values. The responses of the subject can be obtained by providing stimuli to the subject. The value of the test parameter can be, for example, a reciprocal of a time duration for which an individual stimulus is provided (which can also be referred to as a frequency). Administering the psychometric test can include, for example, positioning the subject on a motion platform such as the motion platform 12 described with reference to FIG. 1, and obtaining an estimate of a parameter vector of the subject's psychometric function based on information indicative of the subject's perception of motion in response to a motion profile set. A subsequent motion profile can be selected based on the first estimate.

Operations can also include scaling values from at least one of the plurality of sets using a corresponding scaling function such that the values from the at least two sets of the plurality of sets are mapped on to a unified set (720). In some implementations, the unified data set can include, for example, one of the obtained data sets (e.g., a data set obtained at a particular frequency). In some implementations, the unified data set can be a data set that is different from any of the obtained data sets. Operations also include determining at least one fit parameter that represents a distribution of the scaled values in the unified set (730).

Results

Two models were tested using the new "cross-frequency" fit procedure. Determining fit parameters from the unified dataset was found to be more robust (i.e., fewer failures to fit), more precise (i.e., lower standard deviation for fit parameters), more accurate (i.e., less biased fit parameters), and more efficient (i.e., lower information criterion scores) as compared to determining the fit parameters for individual frequencies.

The technique described here was also found to overcome the underestimation problem by combining all data across frequencies, by directly increasing the number of samples several fold. Specifically, simulations showed that fit based on the unified dataset was more accurate, yielding a five-fold reduction in underestimation (Tables 2 & 3, below). Simulation results also showed that the fit based on the unified dataset reduced failure rate by ten-fold (Table 4 & 5, below) as compared to fits based on individual frequencies, demonstrating increased robustness. By avoiding repeat testing that might result from incorrect fits, the techniques described herein significantly improve overall testing efficiency.

TABLE 2

| Model | $\mu'$ (0°/s) | | $\sigma'$ (1°/s) | | f' (0.4 Hz) | | |
|---|---|---|---|---|---|---|---|
| | mean | std | mean | std | mean | −std | +std |
| 1 | 0.0032 | 0.10 | 0.90 | 0.19 | 0.40 | 0.15 | 0.24 |
| 2 | 0.0034 | 0.10 | 0.90 | 0.16 | 0.40 | 0.12 | 0.17 |
| 3 | 0.0034 | 0.10 | 0.91 | 0.21 | 0.40 | 0.14 | 0.21 |
| 4 | 0.0034 | 0.10 | 0.90 | 0.21 | 0.40 | 0.14 | 0.21 |

TABLE 3

| Model | μ' (0°/s) | | σ' (1°/s) | | f (0.4 Hz) | | |
|---|---|---|---|---|---|---|---|
| | mean | std | mean | std | mean | −std | +std |
| 1 | 0.0032 | 0.092 | 0.98 | 0.18 | 0.40 | 0.13 | 0.19 |
| 4 | 0.0033 | 0.093 | 0.98 | 0.20 | 0.40 | 0.12 | 0.17 |

TABLE 4

| Model | ρ | M | D · (std) | AICc · (std) | BIC · (std) |
|---|---|---|---|---|---|
| #1 | 14 | 978 | 242 · (24) | 272 · (24) | 405 · (25) |
| #2 | 14 | 983 | 243 · (24) | 272 · (24) | 405 · (26) |
| #3 | 14 | 976 | 242 · (24) | 272 · (24) | 405 · (25) |
| #4 | 13 | 979 | 242 · (24) | 270 · (24) | 393 · (25) |

TABLE 5

| Model | ρ | M | D (std) | AICc (std) | BIC (std) |
|---|---|---|---|---|---|
| #1 | 3 | 997 | 240 (21) | 246 (21) | 275 (21) |
| #4 | 3 | 998 | 240 (21) | 246 (21) | 275 (21) |

Simulation results also showed that the fit based on the unified dataset yielded more precise parameter estimates. Specifically, the standard deviations for the estimated parameters were 5% to 20% smaller (Table 3) than for the conventional approach (Table 2). Simulations also showed that the new cross-frequency fitting method required about 10% fewer trials to attain the same precision for an estimated parameter. The cross-frequency fit procedure also yielded better information criterion scores, which were shown to improve between 10% and 30% (Table 5) when compared to the conventional fit procedure (Table 4). The lowered information criterion for the new across-frequency fit procedure were the result of both decreased deviance and fewer parameters.

Reducing Number of Trials by Increasing Difficulty of Individual Trials

In some implementations, if the individual trials are made more difficult or complex, the test becomes more sensitive such that the number of trials required for determining a threshold can be reduced, thereby reducing the overall testing time. In some implementations, an individual trial involving a motion stimulus can be made more difficult by providing a distracting motion prior to the motion stimulus. The distracting motion can be provided, for example, in a direction different than that of the motion stimulus. For example, the distracting motion can be provided in a direction perpendicular to the direction of the motion stimulus (e.g., referring to a Cartesian coordinate system, a distracting motion can be provided in an x direction for a motion stimulus that is provided in the y direction). In some implementations, the distracting motions can be of variable amplitude and frequency, as compared to the motion stimulus.

In some implementations, the individual trial can be made more difficult by asking the subject to include in the response, a confidence rating associated with the subject's perception of the stimuli. In some implementations, testing time is decreased because the inter-time interval between a motion stimulus in one head-centered axis and a subsequent motion stimulus in another head centered axis can be reduced to about or less than 3 seconds. For example, motion profiles may alternate between y-axis translation and z-axis translation with an inter-trial interval of about 2 seconds.

Increasing Efficiency by Recording Confidence Ratings

In some implementations, confidence ratings, which are assigned to their corresponding stimuli, can be used to make individual trials more difficult, improve the quality of collected data and reduce testing time. In some implementations, thresholds of a psychometric test can be determined from a set of binary responses received from the subject. In some implementations, the test can be made more difficult by adding a third option to the binary response. For example, the subject can be asked to choose one of three responses (e.g., "left", "right", or "uncertain") instead of just one of two responses (e.g., "left" and "right"). Then the collected responses can be analyzed using an indecision model such as a three-option model. However, in this approach, the binary response detection analysis cannot be applied due to the additional "uncertain" response.

The disclosed techniques can be used to collect data including confidence ratings such that both the conventional binary detection analysis and indecision analysis can be applied—separately or together—to the collected data.

Figure 7B:
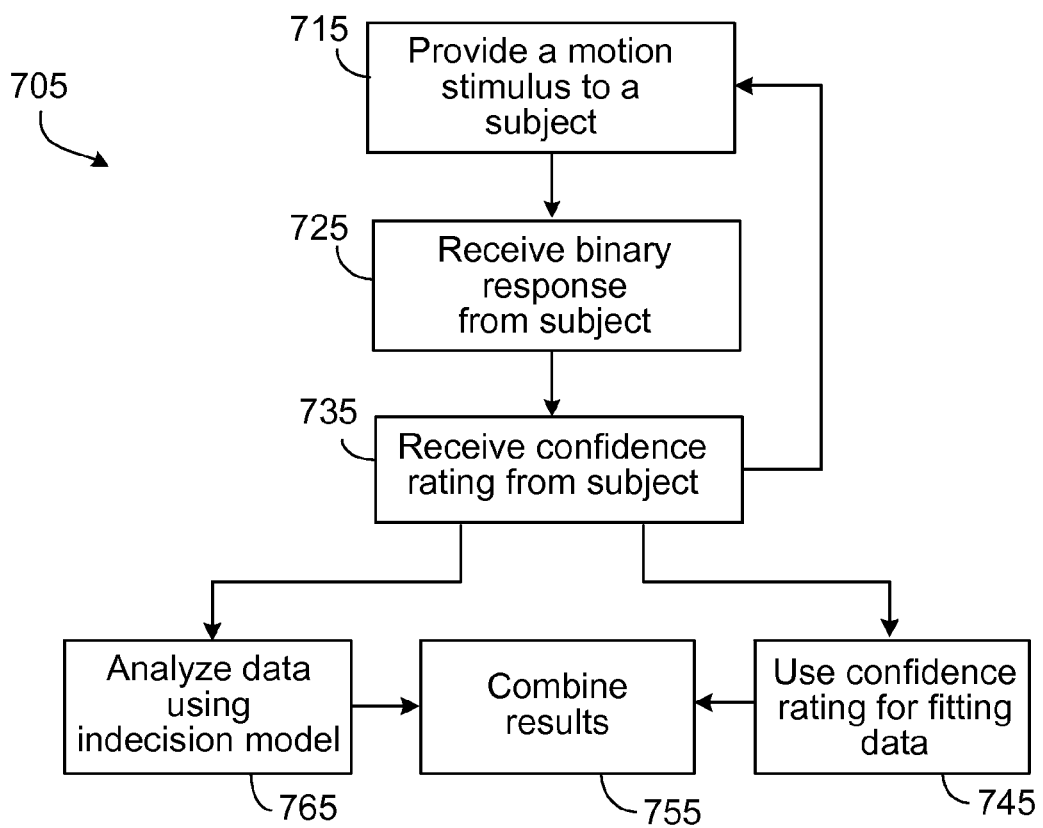
FIG. 7B is a flowchart depicting an example of a sequence of operations for receiving confidence ratings from a subject

Referring to FIG. 7B, a flow chart 705 depicts example operations for receiving confidence ratings. Operations include providing a motion stimulus to a subject (715). In some implementations, the motion can include any of x, y, z translation, roll, pitch, or roll rotation.

Operations also include receiving a binary response from the subject through an input device (725). The binary response can represent the motion perceived by the subject due to the motion stimulus. For example, when the provided motion is a positive translation in the y direction, the subject can input a binary response corresponding to "left" or "right".

Operations further include receiving a confidence rating from the subject through the input device (735). The confidence rating represents how confident the subject is regarding the binary response input. As such, during this operation, the subject can provide an assessment of his or her confidence regarding the perception of the motion stimulus.

The confidence rating can be in any of the following form: (1) a quasi-continuous rating (e.g., 50% confidence to 100% confidence in 1% increments); (2) a binary rating (e.g., "guessing" versus "certain"); (3) a quinary rating (e.g., 1 to 5 where 1 is "guessing" and 5 is "certain") or a N-level discrete rating (e.g., 1 to N where 1 is "guessing" and N is "certain"); or (4) a wagering rating. For example, when the "quasi-continuous rating" is used, the subject can input his or her confidence rating as a percentage value regarding the binary response input. The input confidence rating can be communicated to a processor 16, which can estimate a psychometric function or threshold of the test based on the received data. In some implementations, the operations (715)-(735) can correspond to one trial during the test.

Further operations can be in included in process 710. In some implementations, the following operations can be executed for data (e.g., binary response, confidence rating) obtained from a single trial or data obtained from a plurality of trials. In other words, operations (710)-(730) can be executed once or multiple times before proceeding to the following operations. For each trial, there can be at least one binary response and at least one corresponding confidence rating.

Operations can also include using the received confidence rating during data collection (e.g., for each trial) and/or after data collection is complete (e.g., for multiple trials) for fitting data (745). This can improve the efficiency of the test and fit quality of an estimated psychometric function, which can be estimated either from the binary responses, the confidence ratings, or both. In some implementations, the received confidence ratings can be fit with a cumulative distribution function (e.g., Gaussian cumulative distribution) to provide information on the point of subjective equality (PSE) and/or the width of the distribution (e.g., "sigma") of the estimated psychometric function. For example, an indication that the subject moved in a positive direction with 83% confidence could be equivalent to a probability level of 0.83 on a psychometric function that varies between 0 and 1. An indication that the subject moved in a negative direction with 83% confidence could be equivalent to a probability level of 0.17 for that same psychometric function. Such fits can be useful for determining the parameter (e.g., amplitude, direction, frequency) of the stimulus signal (also may be referred as "stimulus") for the next trial. In other words, the next stimulus can be adapted based on the received confidence rating from the subject.

In some implementations, when the confidence ratings are used, a small number of trials (e.g., 30 or less, 25 or less, 20 or less, 15 or less) can be sufficient to estimate the fit parameters. For such a low number of trials, estimation of the psychometric function using only binary responses can yield large variability in the fit parameters. For example, a psychometric function estimated from 25 from 25 binary responses (from 25 trials) can have a standard deviation of the estimated width parameter (e.g., sigma or (3) to be 50% of the actual value of the width parameter. Fitting accuracy can be improved using the confidence ratings, and the accuracy can be higher than the fitting accuracy of binary responses. In some implementations, the fitting of confidence ratings and binary response can be combined to improve the accuracy. The confidence ratings can be used in a closed-loop manner for estimating the psychometric function and its threshold.

Data collection of confidence ratings can be used to improve the testing efficiency because: (1) a useful stimulus for the next trial can be determined; and/or (2) estimation of the psychometric function can be improved with a small number of trials, thereby reducing testing time. In some implementations, the confidence ratings can provide additional data to validate or invalidate the binary response detection model or the indecision model for different subjects.

Operations may include analyzing the binary response and confidence rating using an indecision model (765). In some implementations, the confidence rating can be used to re-label its corresponding binary response (e.g., "left" or "right") as "uncertain" when the confidence rating is below a confidence threshold. For example, when using a quasi-continuous rating (50% confidence to 100% confidence), the confidence threshold can be set as 55%. In this example, the binary response with confidence rating below 55% can be considered as a guess and re-labeled as "uncertain". As a result, the modified binary responses can include the three options including a binary response (e.g., "left" or "right") and "uncertain". Such modified binary responses can be analyzed using the indecision model.

In some implementations operations may include combining the results (755) obtained via operations 745 and 765. For example, the resulting parameters from operations 745 and 765 can be averaged, or combined using appropriate weights to produce final estimates of the parameters.

Alternatively, in some implementations, the confidence ratings can be used to eliminate binary responses where it is determined that the subject 150 has simply guessed in providing the binary response. For example, when using the quasi-continuous rating (50% confidence to 100% confidence), if a certain binary response has a confidence rating below the confidence threshold (e.g., set as 55%), that binary response can be eliminated from the collected data. As a result, the binary response still includes two options (e.g., "left" or "right"), but the resulting number of binary responses may be reduced due to elimination. Although, the number of binary responses is reduced, the quality of data can improve because only responses that were not guesses were analyzed.

In some implementations, the operations of process 700 can be applied to other types of psychometric tests than vestibular tests. For example, the psychometric tests can be visual tests where the stimuli are visual cues instead of motion.

Synchronization with the Cardiac Cycle

In some implementations, perceptual threshold testing can be improved by synchronizing the motion stimuli with particular points in the subject's cardiac cycle. Cardiac function can impact neural processing. For example, eye movements have been shown to be synchronized to the cardiac cycle in rhesus monkeys with no known vestibular deficits and in humans with semicircular canal dehiscence or fistulas. Cardiac effects can impact the vestibular organs and activate the vestibuloocular reflex. In some implementations, perceptual thresholds for motion recognition can also be impacted by the cardiac cycle. For example, perceptual thresholds can vary by about 10% depending on when in the cardiac cycle they are measured. Therefore, testing efficiency can be improved by providing the motion stimuli at a particular point in the subject's cardiac cycle. In some implementations, such synchronization with cardiac cycles can also be done when estimating other perceptual thresholds (e.g., visual, or auditory perception thresholds). Therefore, the measurement precision can be improved by always providing the motion stimuli at the same part of the cardiac cycle. This can provide the advantage of having to conduct a smaller number of trials for the same measurement precision, thereby reducing the overall testing time.

Overview of a Computing Device

Figure 8:
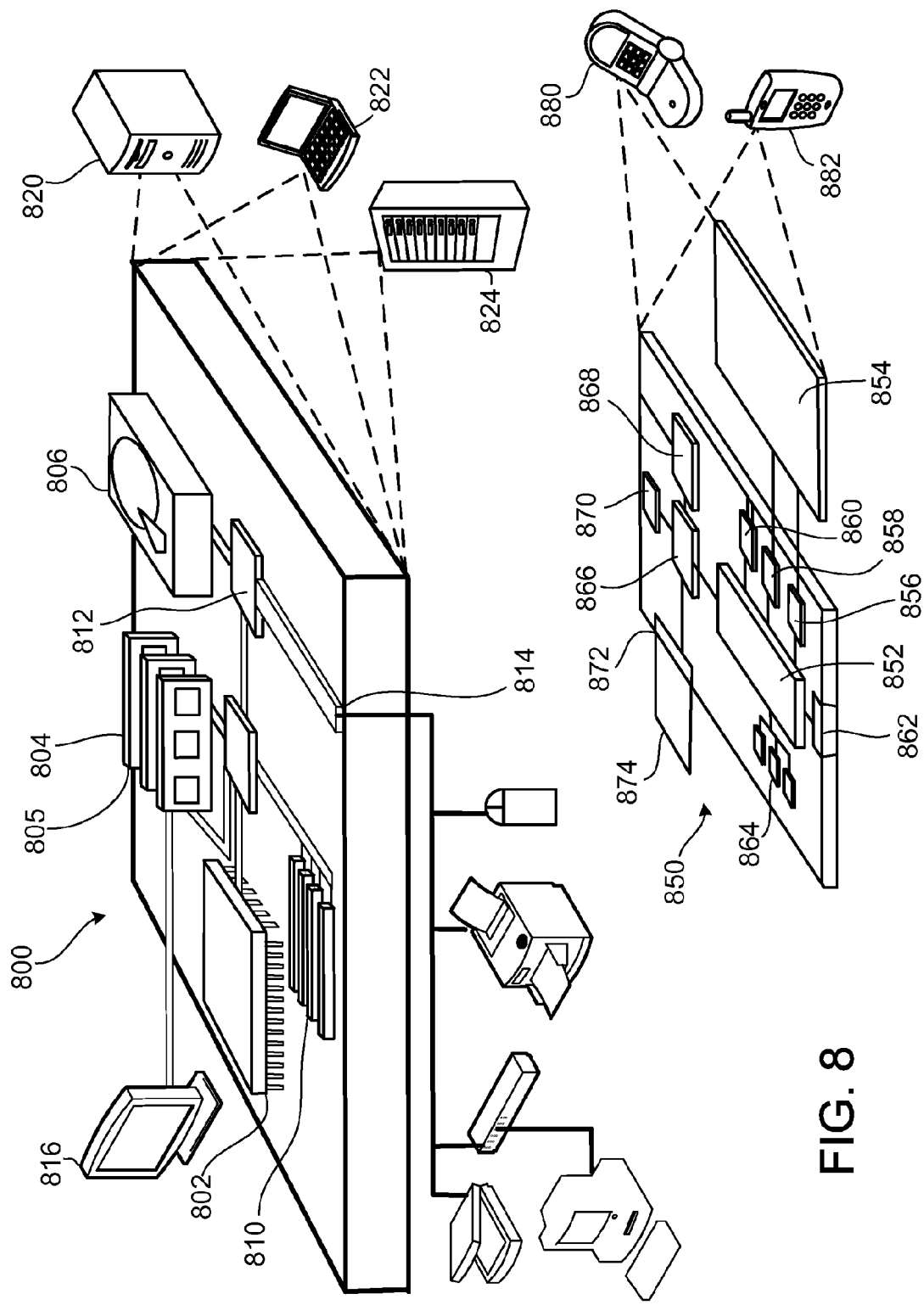
FIG. 8 is a block diagram of a computing device.

FIG. 8 shows an example of a computing device 800 and a mobile device 850, which may be used with the techniques described here. Referring to FIG. 1, the control 14 and the processor 16 can include at least a portion of one or more of the computing device 800 or the mobile device 850. Computing device 800 is intended to represent various forms of digital computers, such as laptops, desktops, workstations, personal digital assistants, servers, blade servers, mainframes, and other appropriate computers. Computing device 850 is intended to represent various forms of mobile devices, such as personal digital assistants, tablet computers, cellular telephones, smartphones, and other similar computing devices. The components shown here, their connections and relationships, and their functions, are meant to be examples only, and are not meant to limit implementations of the techniques described and/or claimed in this document.

Computing device 800 includes a processor 802, memory 804, a storage device 806, a high-speed interface 808 connecting to memory 804 and high-speed expansion ports 810, and a low speed interface 812 connecting to low speed bus 814 and storage device 606. Each of the components 802, 804, 806, 808, 810, and 812, are interconnected using various busses, and may be mounted on a common motherboard or in other manners as appropriate. The processor 802 can process instructions for execution within the computing device 800, including instructions stored in the memory 804 or on the storage device 806 to display graphical information for a GUI on an external input/output device, such as display 816 coupled to high speed interface 808. In other implementations, multiple processors and/or multiple buses may be used, as appropriate, along with multiple memories and types of memory. Also, multiple computing devices 800 may be connected, with each device providing portions of the necessary operations (e.g., as a server bank, a group of blade servers, or a multi-processor system). In some implementations the computing device can include a graphics processing unit.

The memory 804 stores information within the computing device 800. In one implementation, the memory 804 is a volatile memory unit or units. In another implementation, the memory 804 is a non-volatile memory unit or units. The memory 804 may also be another form of computer-readable medium, such as a magnetic or optical disk.

The storage device 806 is capable of providing mass storage for the computing device 800. In one implementation, the storage device 806 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 804, the storage device 806, memory on processor 802, or a propagated signal.

The high speed controller 808 manages bandwidth-intensive operations for the computing device 800, while the low speed controller 812 manages lower bandwidth-intensive operations. Such allocation of functions is an example only. In one implementation, the high-speed controller 808 is coupled to memory 804, display 816 (e.g., through a graphics processor or accelerator), and to high-speed expansion ports 810, which may accept various expansion cards (not shown). In the implementation, low-speed controller 812 is coupled to storage device 806 and low-speed expansion port 814. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 800 may be implemented in a number of different forms, as shown in the figure. For example, it may be implemented as a standard server 820, or multiple times in a group of such servers. It may also be implemented as part of a rack server system 824. In addition, it may be implemented in a personal computer such as a laptop computer 822. Alternatively, components from computing device 800 may be combined with other components in a mobile device, such as the device 850. Each of such devices may contain one or more of computing device 800, 850, and an entire system may be made up of multiple computing devices 800, 850 communicating with each other.

Computing device 850 includes a processor 852, memory 864, an input/output device such as a display 854, a communication interface 866, and a transceiver 868, among other components. The device 850 may also be provided with a storage device, such as a microdrive or other device, to provide additional storage. Each of the components 850, 852, 864, 854, 866, and 868, are interconnected using various buses, and several of the components may be mounted on a common motherboard or in other manners as appropriate.

The processor 852 can execute instructions within the computing device 850, including instructions stored in the memory 864. The processor may be implemented as a chipset of chips that include separate and multiple analog and digital processors. The processor may provide, for example, for coordination of the other components of the device 850, such as control of user-interfaces, applications run by device 850, and wireless communication by device 850.

Processor 852 may communicate with a user through control interface 858 and display interface 856 coupled to a display 854. The display 854 may be, for example, a TFT LCD (Thin-Film-Transistor Liquid Crystal Display) or an OLED (Organic Light Emitting Diode) display, or other appropriate display technology. The display interface 856 may comprise appropriate circuitry for driving the display 854 to present graphical and other information to a user. The control interface 858 may receive commands from a user and convert them for submission to the processor 852. In addition, an external interface 862 may be provide in communication with processor 852, so as to enable near area communication of device 850 with other devices. External interface 862 may provide, for example, for wired communication in some implementations, or for wireless communication in other implementations, and multiple interfaces may also be used.

The memory 864 stores information within the computing device 850. The memory 864 can be implemented as one or more of a computer-readable medium or media, a volatile memory unit or units, or a non-volatile memory unit or units. Expansion memory 874 may also be provided and connected to device 850 through expansion interface 872, which may include, for example, a SIMM (Single In Line Memory Module) card interface. Such expansion memory 874 may provide extra storage space for device 850, or may also store applications or other information for device 850. Specifically, expansion memory 874 may include instructions to carry out or supplement the processes described above, and may include secure information also. Thus, for example, expansion memory 874 may be provide as a security module for device 850, and may be programmed with instructions that permit secure use of device 850. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 864, expansion memory 874, memory on processor 852, or a propagated signal that may be received, for example, over transceiver 868 or external interface 862.

Device 850 may communicate wirelessly through communication interface 866, which may include digital signal processing circuitry where necessary. Communication interface 866 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 868. In addition, short-range communication may occur, such as using a Bluetooth, WiFi, or other such transceiver (not shown). In addition, GPS (Global Positioning System) receiver module 870 may provide additional navigation- and location-related wireless data to device 850, which may be used as appropriate by applications running on device 850.

Device 850 may also communicate audibly using audio codec 860, which may receive spoken information from a user and convert it to usable digital information. Audio codec 860 may likewise generate audible sound for a user, such as through a speaker, e.g., in a handset of device 850. Such sound may include sound from voice telephone calls, may include recorded sound (e.g., voice messages, music files, and so forth) and may also include sound generated by applications operating on device 850.

The computing device 850 may be implemented in a number of different forms, as shown in the figure. For example, it may be implemented as a cellular telephone 880. It may also be implemented as part of a smartphone 882, personal digital assistant, tablet computer, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well. For example, feedback provided to the user can be any form of sensory feedback (e.g., visual feedback, auditory feedback, or tactile feedback). Input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user-interface or a Web browser through which a user can interact with an implementation of the systems and techniques described here), or any combination of such back end, middleware, or front end components. The components of the system can be interconnected by any form or medium of digital data communication. Examples of networks include a local area network ("LAN"), a wide area network ("WAN"), and the Internet.

The computing system can include clients and servers. A client and server are generally remote from each other and typically interact through a communication network such as the network 102. The relationship of client and server arises by virtue of computer programs running on the respective computers and having a client-server relationship to each other.

EXAMPLES

Analyses and simulations were performed to show that high efficiency can be attained when stimuli are provided at levels that yield a target percentage (e.g. 80% to 95%) of correct responses. Various staircase procedures can be used various target percentages. For example, one-down/one-up staircase (1D/1U) is designed to produce 50% correct responses on average. As another example, a two-down/one-up (2D/1U) staircase is designed to produce 70.7% correct responses. In another example, a 3D/1U staircase is designed to produce 79.7% correct responses, and a 4D/1U staircase is designed to produce 84.1% correct responses. A set of rules known as "parameter estimation by sequential testing" (PEST) were utilized for designing these symmetric staircases, where symmetric refers to the fact that the upward and downward steps were the same size. Therefore, this example is referred to as a "cross-frequency symmetric staircase."

Asymmetric staircases that utilize different upward and downward step sizes were also used for different target percentages. These will be referred to as "cross-frequency asymmetric staircases." For asymmetric staircases, the upward step sizes were different from the downward step sizes. Denoting the up step size as U and the down step size as D, and assuming D=1 (since the ratio U/D is of interest), the staircase parameters can be calculated as follows. For a 1D/1U staircase, the target percentage correct (p) and staircase step sizes U and D can be related as:

$$pD=qU=(1-p)U$$

where q is the percent incorrect, and equals to (1−p). In one example, if p=0.9, the ratio of U/D can be calculated to be equal to 9. For a 2D/1U staircase, the relation between U and D can be represented by the equation:

$$ppD=(1-p)U+p(1-p)U$$

In one example, if p=0.9, the ratio of U/D can be calculated to equal 4.26. For a 3D/1U staircase, the relevant equation can be represented as:

$$pppD=(1-p)U+p(1-p)U+pp(1-p)U$$

Therefore, for p=0.9, the ratio of U/D can be calculated to equal 2.69.

A 3D/1U staircase yielded 70.7% correct responses on average when upward and downward steps were symmetric. However, when the upward steps were 2.69 times the size of the downward steps, this set an average target stimulus that yielded 90% correct responses on average.

In some cases, a larger step size was used when a mistake was made on the first trial than when a mistake was made on the third trial, resulting in different upward step sizes.

The maximum likelihood approach to target stimulus levels was generalized across frequencies, and is referred to herein as the "cross-frequency fitted sampling method." The following procedures were used.

Cross-Frequency Symmetric Staircase

This procedure utilized standard staircase procedures (i.e., 2D/1U, 3D/1U, 4D/1U, etc.) with symmetric upward and downward step sizes. The current example used a modified four-down/1-up (4D/1U) staircase procedure with PEST rules guiding the step sizes. Specifically, the motion velocity or amplitude decreased every time the subject correctly reported the motion direction four times in a row ("4 down"), and the motion velocity increased anytime the subject incorrectly reported motion direction ("1 up"). Testing began at 1 Hz and proceeded until the subject established a minimum (1 "wrong") followed by a maximum (four "correct") at 1 Hz. Testing then proceeded to the next higher frequency (1.2 Hz) until a minimum (1 wrong) was established at that frequency. Testing then proceeded at the next frequency (1.71 Hz) until a maximum was established. This pattern of interleaved "maximal extrema" and "minimal extrema" continued, incrementing the frequency after each extrema, until the subject had established a minimal and maximal extrema at each frequency (in this case 0.10, 014, 0.20, 0.29, 0.41, 0.59, 1.00, 1.20, 1.71, 2.50, 3.53, 5.00 Hz). This was accomplished by increasing the frequency from 1 Hz to 5 Hz then decreasing to 0.1 Hz, and then again increasing to 1 Hz. This sampling method, when combined with the cross-frequency and bias-reduction fits described earlier, yielded threshold estimates as a function of frequency matching those obtained with more extensive data collections that require 2 hours as opposed to the much shorter duration of time (e.g., about 3 minutes for translational motion, or about 19 minutes for roll tilt motion) needed for the current example.

Cross-Frequency Asymmetric Staircases

A cross-frequency asymmetric staircase mimics the cross-frequency symmetric staircase described above, except that the upward steps have a different size than the downward steps. Specifically, in the cross-frequency asymmetric staircase procedure, the upward step sizes were made to be larger than the downward step sizes, such that the average stimulus was closer to the desired target stimulus level. However, the upward step sizes were substantially similar to one another regardless of whether the subject made a mistake in the first trial or a subsequent trial. In some tests, for a given stimulus level, larger step sizes were used for upward stimuli that followed a mistake in the first trial than for a mistake made in the second (or subsequent) trials. As for the cross-frequency symmetric staircase, extrema were determined at different frequencies and the stimuli were provided at the next frequency after each extrema.

Cross-Frequency Fitted Curve

In the cross-frequency fitted curve method, the frequency was changed to the next nearby frequency sequentially with each adaptive track extrema. For each frequency, the stimulus amplitude was determined using the unified dataset method described above. In this procedure, a fit was determined using all available data and then the fitted function was used to select the desired motion stimuli for a given frequency and target percentage.

To compare the various procedures, the simulations were stopped when 150 trials were completed. Simulation results summarized in Table 6 shows that, on average, larger upward step sizes (as compared to the downward step sizes) led to improved performance that was manifested as reduced threshold ($\sigma$) biases at various frequencies, and reduced threshold variances at various frequencies. On average, the 4D/1U staircase yielded better performance than the 5D/1U, 3D/1U and 2D/1U staircases. The 4D/1U cross-frequency symmetric staircase yielded better results than a 4D/1U cross-frequency symmetric staircase. Also having different upward step sizes did not yield any significant benefits as compared to maintaining the same upward step size independent of when the incorrect response was being provided.

While the above tests were performed for vestibular applications, the results can be generalized to other threshold testing scenario where thresholds vary as a function of some parameter (or parameters) in a way that can be quantified and modeled. The methods described in the application can be applied to psychophysical tests of vision, hearing, and touch (pain). For example, the techniques described in this document can be used for estimating visual thresholds that vary as a function of retinal location. Automated perimetry is used to measure visual thresholds at a large number of locations. When modeled quantitatively, the techniques described in this document can be used for automated perimetry applications. For example, a two-parameter model can be developed to include horizontal and vertical displacements. As another example, visual thresholds that vary as a function of light frequency (i.e., "color") can also be estimated using the techniques described in this document.

TABLE 6

| Same step | Down step | Up step | | | | | Different step | Down step | Up step | | | | |
| --- | --- | --- | --- | --- | --- | --- | --- | --- | --- | --- | --- | --- | --- |
| | | X | OX | OOX | OOOX | OOOOX | | | X | OX | OOX | OOOX | OOOOX |
| a5D1U | 1 | 1.442 | 1.442 | 1.442 | 1.442 | 1.442 | a5D1U | 1 | 2.246 | 1.797 | 1.348 | 0.899 | 0.449 |
| a4D1U | 1 | 1.908 | 1.908 | 1.908 | 1.908 | | a4D1U | 1 | 2.900 | 2.175 | 1.450 | 0.725 | |
| a3D1U | 1 | 2.690 | 2.690 | 2.690 | | | a3D1U | 1 | 3.899 | 2.599 | 1.300 | | |
| a2D1U | 1 | 4.263 | 4.263 | | | | a2D1U | 1 | 5.586 | 2.793 | | | |

| | $\mu(0)$ | SD | $\sigma(1)$ | SD | fc(0.4) | SD | Available Data | D | SD |
| --- | --- | --- | --- | --- | --- | --- | --- | --- | --- |
| 250 trials, brglmfit | | | | | | | | | |
| 2D1U | 0.000 | 0.111 | 0.933 | 0.302 | 0.450 | 0.673 | 8163 | 165.13 | 7.75 |
| a2D1U_same step | 0.003 | 0.166 | 1.006 | 0.247 | 0.401 | 0.338 | 9716 | 74.11 | 4.67 |
| a2D1U_different step | 0.002 | 0.168 | 1.012 | 0.252 | 0.398 | 0.323 | 9668 | 72.71 | 6.17 |
| 3D1U | 0.002 | 0.123 | 0.973 | 0.251 | 0.408 | 0.456 | 9026 | 132.59 | 8.27 |
| a3D1U_same step | 0.001 | 0.160 | 1.006 | 0.230 | 0.394 | 0.288 | 9736 | 77.49 | 5.01 |
| a3D1U_different step | 0.006 | 0.163 | 1.008 | 0.235 | 0.395 | 0.303 | 9769 | 75.94 | 6.36 |

TABLE 6-continued

| | | | | | | | | | |
|---|---|---|---|---|---|---|---|---|---|
| 4D1U | 0.000 | 0.131 | 0.985 | 0.246 | 0.400 | 0.355 | 9535 | 117.17 | 7.57 |
| a4D1U_same step | 0.002 | 0.155 | 1.008 | 0.217 | 0.388 | 0.281 | 9728 | 81.12 | 5.07 |
| a4D1U_different step | 0.001 | 0.159 | 1.008 | 0.221 | 0.392 | 0.298 | 9660 | 79.53 | 6.38 |
| 5D1U | 0.002 | 0.135 | 0.994 | 0.225 | 0.392 | 0.326 | 9537 | 108.82 | 7.46 |
| a5D1U_same step | 0.000 | 0.154 | 1.002 | 0.218 | 0.393 | 0.359 | 9418 | 83.31 | 4.57 |
| a5D1U_different step | 0.001 | 0.155 | 1.002 | 0.213 | 0.394 | 0.360 | 9378 | 81.23 | 5.42 |
| 150 trials, brglmfit | | | | | | | | | |
| 2D1U | 0.000 | 0.118 | 0.974 | 0.361 | 0.272 | 9.938 | 10000 | 165.67 | 7.72 |
| a2D1U_same step | 0.002 | 0.168 | 1.018 | 0.257 | 0.376 | 0.441 | 10000 | 74.15 | 4.68 |
| a2D1U_different step | 0.002 | 0.170 | 1.027 | 0.264 | 0.368 | 0.412 | 10000 | 72.80 | 6.20 |
| 3D1U | 0.002 | 0.128 | 0.998 | 0.276 | 0.315 | 4.509 | 10000 | 133.25 | 8.48 |
| a3D1U_same step | 0.001 | 0.161 | 1.017 | 0.240 | 0.372 | 1.052 | 10000 | 77.53 | 5.00 |
| a3D1U_different step | 0.006 | 0.165 | 1.058 | 0.244 | 0.374 | 0.306 | 10000 | 75.97 | 6.36 |
| 4D1U | 0.000 | 0.133 | 1.001 | 0.262 | 0.359 | 2.330 | 10000 | 117.31 | 7.61 |
| a4D1U_same step | 0.002 | 0.157 | 1.018 | 0.226 | 0.362 | 0.309 | 10000 | 81.10 | 5.06 |
| a4D1U_different step | 0.001 | 0.160 | 1.019 | 0.229 | 0.354 | 0.320 | 10000 | 79.48 | 6.35 |
| 5D1U | 0.002 | 0.138 | 1.008 | 0.237 | 0.347 | 1.200 | 10000 | 108.58 | 7.61 |
| a5D1U_same step | 0.000 | 0.157 | 1.017 | 0.228 | 0.320 | 1.120 | 10000 | 83.00 | 4.72 |
| a5D1U_different step | 0.001 | 0.159 | 1.019 | 0.223 | 0.317 | 1.324 | 10000 | 80.97 | 5.51 |

| | 1 Hz (1.4) | SD | 5 Hz (1.08) | SD | 0.1 Hz (5) | SD | Time | SD |
|---|---|---|---|---|---|---|---|---|
| 250 trials, brglmfit | | | | | | | | |
| 2D1U | 1.452 | 0.280 | 1.047 | 0.278 | 5.386 | 2.481 | 13.56 | 0.96 |
| a2D1U_same step | 1.460 | 0.200 | 1.101 | 0.229 | 5.182 | 1.472 | 13.16 | 0.75 |
| a2D1U_different step | 1.466 | 0.206 | 1.107 | 0.235 | 5.181 | 1.462 | 13.28 | 0.80 |
| 3D1U | 1.438 | 0.213 | 1.072 | 0.230 | 5.129 | 1.896 | 13.15 | 0.93 |
| a3D1U_same step | 1.446 | 0.189 | 1.097 | 0.215 | 5.092 | 1.352 | 13.47 | 0.90 |
| a3D1U_different step | 1.452 | 0.194 | 1.100 | 0.220 | 5.121 | 1.404 | 13.52 | 0.88 |
| 4D1U | 1.433 | 0.202 | 1.079 | 0.228 | 5.079 | 1.515 | 14.12 | 1.01 |
| a4D1U_same step | 1.442 | 0.182 | 1.098 | 0.202 | 5.046 | 1.407 | 13.37 | 1.10 |
| a4D1U_different step | 1.446 | 0.185 | 1.099 | 0.205 | 5.078 | 1.419 | 13.32 | 1.13 |
| 5D1U | 1.433 | 0.193 | 1.086 | 0.208 | 5.034 | 1.596 | 13.63 | 1.55 |
| a5D1U_same step | 1.448 | 0.182 | 1.096 | 0.199 | 5.085 | 1.699 | 12.58 | 1.55 |
| a5D1U_different step | 1.448 | 0.180 | 1.095 | 0.193 | 5.092 | 1.719 | 12.47 | 1.53 |
| 150 trials, brglmfit | | | | | | | | |
| 2D1U | 1.527 | 0.300 | 1.124 | 0.320 | 4.879 | 3.296 | 13.53 | 0.96 |
| a2D1U_same step | 1.466 | 0.201 | 1.112 | 0.237 | 5.076 | 1.542 | 13.16 | 0.75 |
| a2D1U_different step | 1.472 | 0.207 | 1.120 | 0.244 | 5.053 | 1.539 | 13.28 | 0.80 |
| 3D1U | 1.454 | 0.219 | 1.103 | 0.248 | 4.767 | 2.227 | 13.20 | 0.94 |
| a3D1U_same step | 1.452 | 0.190 | 1.108 | 0.223 | 5.002 | 1.417 | 13.46 | 0.89 |
| a3D1U_different step | 1.456 | 0.195 | 1.109 | 0.226 | 5.029 | 1.458 | 13.52 | 0.89 |
| 4D1U | 1.444 | 0.204 | 1.096 | 0.240 | 4.922 | 1.667 | 14.09 | 1.02 |
| a4D1U_same step | 1.445 | 0.183 | 1.107 | 0.208 | 4.933 | 1.480 | 13.36 | 1.12 |
| a4D1U_different step | 1.447 | 0.186 | 1.108 | 0.211 | 4.920 | 1.519 | 13.28 | 1.17 |
| 5D1U | 1.438 | 0.195 | 1.099 | 0.217 | 4.849 | 1.765 | 13.56 | 1.58 |
| a5D1U_same step | 1.446 | 0.185 | 1.109 | 0.205 | 4.796 | 1.893 | 12.48 | 1.60 |
| a5D1U_different step | 1.446 | 0.183 | 1.110 | 0.200 | 4.778 | 1.915 | 12.36 | 1.58 |

Figures 9A, 9B, 9C:
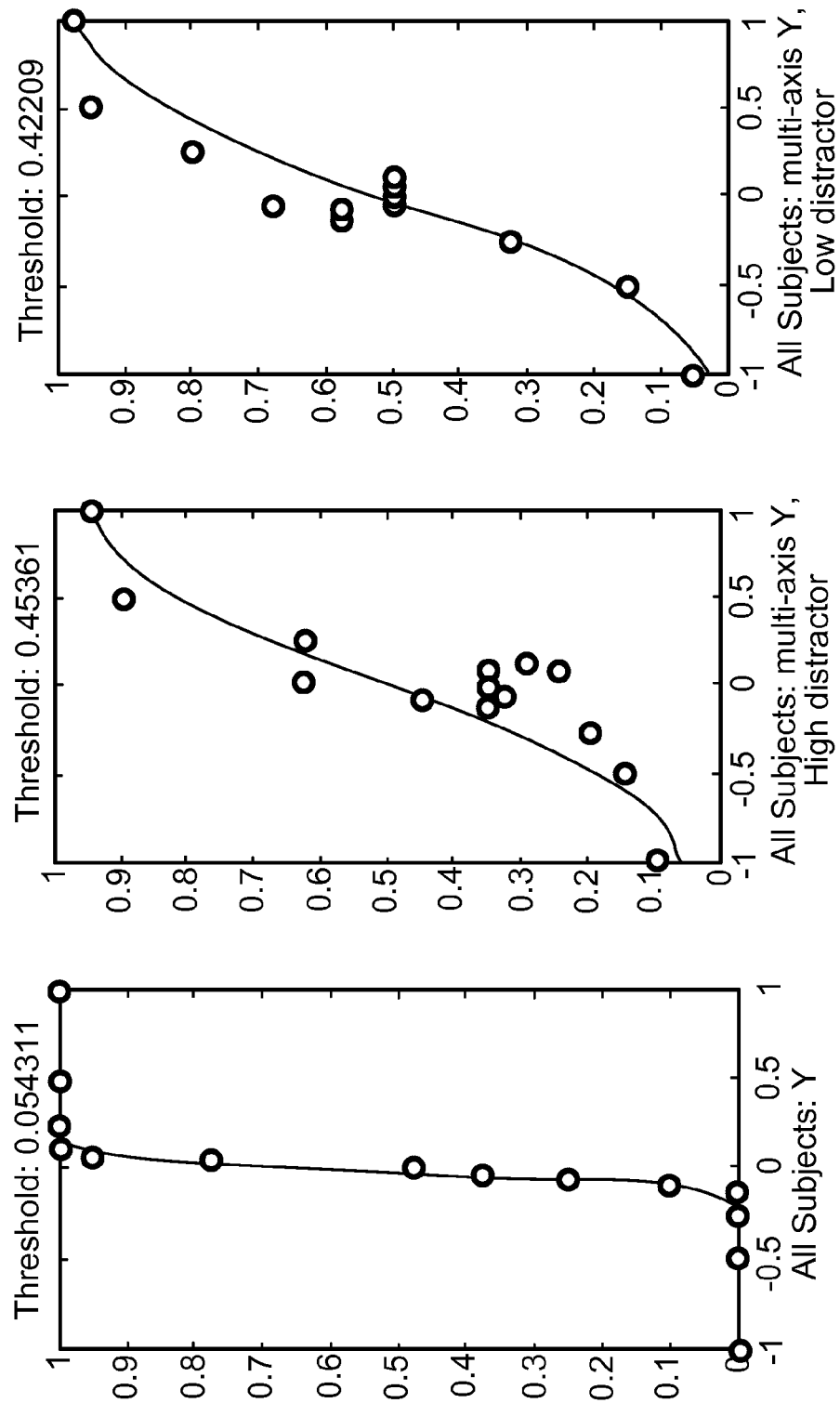
FIGS. 9A-9C show some example plots illustrating effects of providing distracting motions prior to providing motion stimuli.

In another experiment, the effect of a distracting motion prior to providing a motion stimulus, was tested. In this case, four subjects were provided with a series of ten sequential single-cycle sinusoidal (5 Hz) acceleration motion stimuli—each 0.2 s in duration. One of these was translation to the left or right (y-axis direction recognition task) that varied in acceleration amplitude between −1 m/s/s to +1 m/s/s. Eight of the ten motion stimuli included two pitch tilts (0.1° each, which corresponds to a peak velocity of 2°/s and angular acceleration magnitude of 32°/s/s), two roll tilts (0.1° each), two yaw rotations (0.1° each), and two z-axis translations (0.6 mm each, which corresponded to a peak velocity of 6.4 mm/s and acceleration magnitude of 200 mm/s/s). The other motion was a forward/backward translation, which was either 0.6 mm ("low-amplitude") or 1.2 mm ("high-amplitude"). The peak velocity of the x-axis motion always preceded the peak velocity of the y-axis motion by 0.2, 0.4, 0.6, 0.8, or 1.0 s. Translations along the x-axis or y-axis were never first or last. The results for the y-axis translation threshold are shown in FIGS. 9A-C. All rotations were about axes that intersected in the middle of the head at the level of the ears. Each of these motion stimuli was above the threshold measured when the stimuli were provided individually.

FIGS. 9A-C show average y-translation psychometric function across the four subjects for 3 different conditions. FIG. 9A is a plot obtained with no preceding distracting motion. The plot in FIG. 9B was obtained with a high-amplitude x-axis distracting motions, and the plot in FIG. 9C was obtained with low-amplitude x-axis distracting motions. Thresholds for y-translation with high-amplitude and low-amplitude distracting motions were indistinguishable and were both substantially greater than the threshold obtained with no preceding motion. In this example, the threshold was 0.05 m/s/s (0.32 m/s peak velocity) when the y-translation was presented in isolation. The thresholds were 0.45 m/s/s (2.87 cm/s) and 0.42 m/s/s (2.68 cm/s) when preceded by a high-amplitude or low-amplitude distracting motion, respectively. These results demonstrate that the y-translation threshold increased by almost an order of magnitude when immediately preceded by threshold-level motion in directions other than the y-axis translation threshold that was assayed.

In another experiment, the relationship between vestibular testing efficiency and the subject's cardiac cycle was tested. In this case, yaw perceptual thresholds were measured with motions that always occur at the same part of the cardiac cycle. The motions lasted 0.2 s (i.e., the frequency was 5 Hz) to provide fine resolution within the cardiac cycle. Thresholds were measured with motion stimuli provided at 0, 0.1, 0.2, 0.3, 0.4 or 0.6 s after the QRS complex, i.e., the combination of three graphical deflections in an electrocardiogram (ECG) representation of the subject's cardiac cycle. Each threshold was calculated using sixty trials. Each set of the sixty trials took approximately 7 minutes to acquire, which also included a short break. Therefore, seven thresholds, one for each delay, were acquired in a one-hour session, including preparation time.

Figure 10:
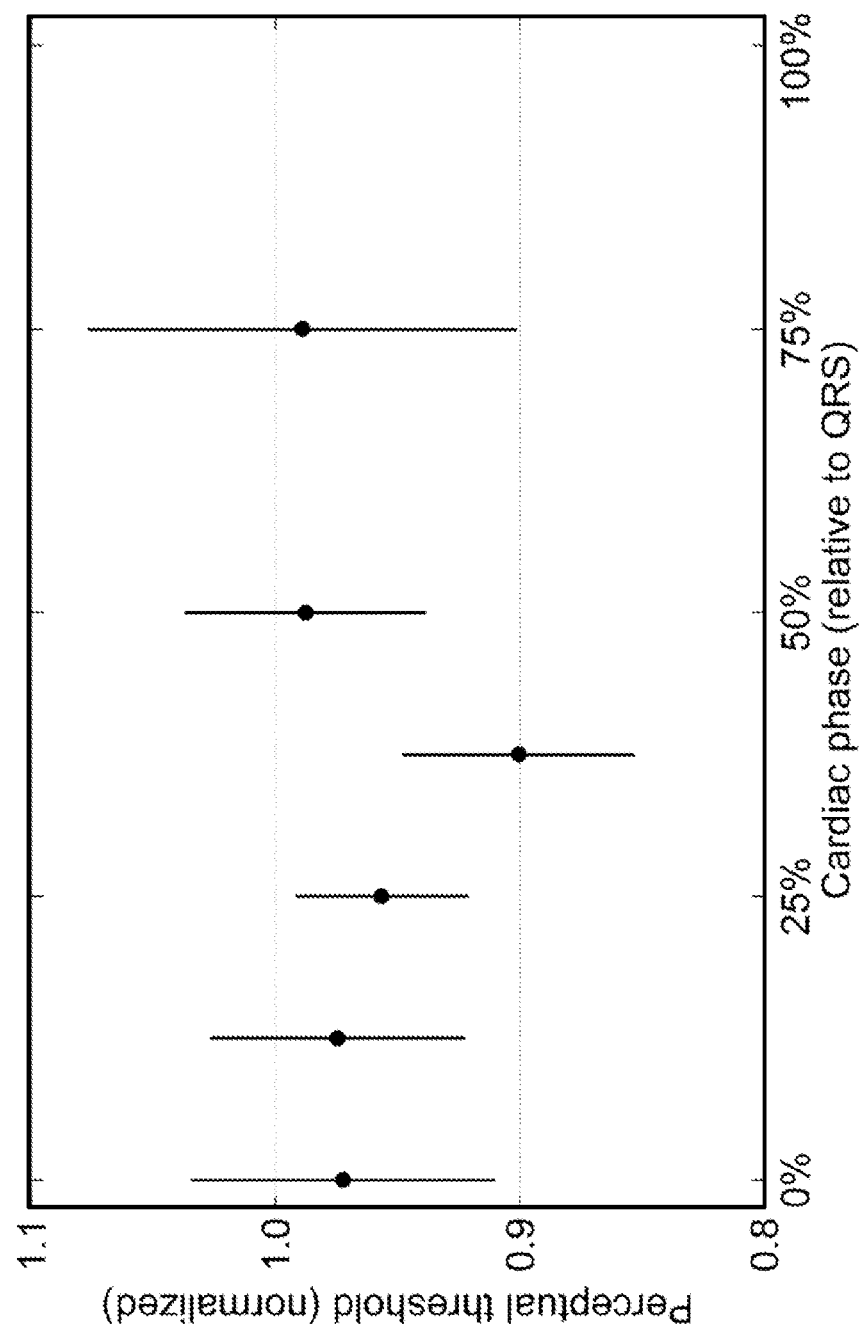
FIG. 10 shows an example of a relationship between perceptual thresholds and cardiac cycles.

FIG. 10 shows perceptual thresholds at different parts of the cardiac cycle, collected using the proposed approach. The thresholds shown in FIG. 10 are an average of 12 subjects. The threshold was found to be 9% lower when synchronized with a delay of 0.3 s (38% cardiac phase) than when synchronized with a 0.4 s delay (50% cardiac phase). The error bars shown in in FIG. 10 are smaller at certain parts of the cardiac cycle, indicating a more precise measurement of threshold, even though all thresholds measurements were based on sixty trials. From FIG. 10, the thresholds were found to vary during the cardiac cycle. Therefore, if the trials are conducted at random parts of the cardiac cycle, the measured thresholds would be expected to vary. Therefore, the measurement precision can be improved by always providing the motion stimuli at the same part of the cardiac cycle. This can provide the advantage of having to conduct a smaller number of trials for the same measurement precision, thereby reducing the overall testing time. Further the variability can be improved as compared to the case when the thresholds are determined by providing the motion stimuli at random points of the cardiac cycle.

In this experiment, normal human subjects were tested to reduce the chances of potential biases due to particular clinical disorders. The human subjects were tested using standard prescreening techniques, visual-vestibular interaction, and/or posture control (12; 13) measures. To reduce potential variability due to age, subjects were selected to be 18-65 years old. The motion stimuli were provided using a MOOG 6DOF2000E motion platform that is capable of providing motion in all six directions (3 rotational, 3 translational). The subjects were seated in a chair with a five-point harness, and a firm, yet comfortable, adjustable head restraint. To eliminate visual influence, all testing was performed in the dark. To minimize the influence of nonvestibular cues on motion direction, all skin surfaces other than the face were covered, noise-cancelling headphones were used to played noise, and tactile cues were reduced using cushions. The motion stimuli included a single cycle of sinusoidal acceleration $[a(t)=A \sin(2\pi ft)=A \sin(2\pi t/T)]$, where A is the acceleration amplitude and f is the frequency, which is the inverse of the period (and duration) of the stimulus (T=1/f). Because the motion began at zero velocity, integration of the acceleration yielded an oscillatory velocity, $v(t)=AT/(2\pi)[1-\cos(2\pi t/T)]$, and a total lateral displacement $\Delta p(t)=AT/(2\pi)[t-T/(2\pi)\sin(2\pi t/T)]$. Therefore, both the peak velocity ($v_{max}=AT/\pi$) and the total lateral displacement ($\Delta p_{total}=AT^2/2\pi$) were proportional to the peak acceleration. Both velocity and displacement were unidirectional. These motion profiles were chosen because they have no acceleration, velocity, or position discontinuities, their spectral content is clearly defined, and they mimic natural volitional head movements.

To measure perceptual thresholds, adaptive, one-interval, categorical, two-alternative, forced-choice, direction-recognition paradigms were used, wherein the subjects had to indicate one of two directions of motion (e.g., translation left or translation right) and had to guess a level of certainty for their choice. Adaptive stimuli based on the subject's responses were provided. Forced choice means that the subject had to provide an answer—guessing if necessary. Categorical refers to the fact that the subject had to classify the response into one category or another (e.g., left/right). Two alternative means that the subject had to make a binary decision for each trial. Direction recognition means that the subject indicated the perceived motion direction. Because the subject knew the possible directions of motion in advance, the subject was allowed to focus full attention on the applied motion (e.g., yaw rotation). Brief tones indicated the starting and ending points of the motion stimulus thereby prompting the subject to indicate their perception of the motion. Subjects indicated their perceived direction of motion using buttons, which was recorded via a computer. A three-down/one-up (3D/1U) staircase procedure was used to determine which stimuli to provide. In this procedure the motion amplitude was decreased by some amount every time the subject correctly recognized the motion direction three times in a row ("three-down"), and the motion amplitude was increased anytime the subject incorrectly indicated the motion direction ("one-up"). This was followed by parameter estimation by sequential estimation (PEST) rules. Initial amplitude used was 4°/s.

Thresholds were determined using standard psychophysical methodologies. First, the proportion of trials (P) in which the subjects reported leftward rotations was plotted against the acceleration level. The obtained data was fitted with a Gaussian cumulative distribution function using a generalized linear model. The fit parameters for the Gaussian distribution were the mean value ($\mu$), which in this case represented any potential vestibular bias (e.g., left/right bias), the standard deviation ($\sigma$), which represented subject uncertainty ("noise"), and a lapse rate ($\lambda$), which accounted for stimulus-independent errors caused by subject lapses (e.g. due to lack of attention or forgetfulness) or other mistakes. The lapse rate was restricted to small values ($0<\lambda<0.05$). Precision was defined as the inverse of the threshold for $\sigma$, i.e., as $1/\sigma$.

The ECG of the subject was recorded using a standard, electrically isolated electrocardiograph (WPI ISO-DAMS) that amplified potentials in the standard "Lead I" configuration with electrodes (3M Red Dot 2560) placed near the right and left shoulder ("RA" and "LA", respectively). A threshold detector detected the QRS complex, and the threshold was adjusted for each subject to be approximately 90% of the amplitude of the R wave. The detector sent a debounced digital pulse to a computer to provide the motion stimulus by triggering platform motion.

Other Embodiments

While a number of implementations have been described, the foregoing description is intended to illustrate and not limit the scope of the appended claims. The systems and techniques described herein can be used in conjunction with parameter estimation in other types of test where a stimulus is provided to a subject and a response of the subject is analyzed to estimate the parameter. Other aspects, advantages, and modifications are within the scope of the following claims.

The invention claimed is:

1. A method for assessing a subject's vestibular system, the method comprising:
    administering a psychometric test to a subject and measuring responses of the subject to obtain a set of values, wherein administering the psychometric test comprises:
    positioning the subject on a motion platform that includes a device for supporting the subject and is configured to execute motion profiles,
    obtaining a first estimate of a parameter vector of the subject's psychometric function based on the subject's perception of motion in response to a first motion profile set wherein the subject's perception of motion is received using one or more input devices, and
    adaptively selecting, using one or more processing devices, a subsequent motion profile based at least in part on the first estimate, determining at least one fit parameter that represents a distribution of the set of values and represents a characteristic of the subject's responses to the psychometric test;
    estimating a bias quantity associated with each said fit parameter; subtracting the bias quantity from each said fit parameter to obtain a bias-reduced estimate of the fit parameter;
    scaling the bias-reduced estimate of the fit parameter by a scale-factor to obtain a final estimate of the fit parameter; and
    generating a quantitative measure representing the subject's vestibular system based on the final estimate of the fit parameter.

2. The method of claim 1, wherein the scale factor has a value substantially equal to or less than one.

3. The method of claim 1, wherein the responses of the subject are measured for stimuli corresponding to a plurality of values of a test parameter associated with the motion profiles and the responses to different values of the test parameter are scaled using a corresponding scaling function to obtain the set of values.

4. The method of claim 1, wherein the responses of the subject are obtained by providing a stimulus to the subject for a predetermined number of times to measure the responses of the subject, wherein a level of the stimulus is associated with a corresponding motion profile.

5. The method of claim 1, wherein the distribution is represented as a cumulative distribution function.

6. The method of claim 1, wherein the at least one fit parameter is determined using a numerical maximum-likelihood method.

7. The method of claim 1, wherein the bias quantity represents a first order asymptotic bias.

8. The method of claim 1, further comprising selecting the subsequent motion profile to reduce uncertainty in the estimate.

9. The method of claim 1, further comprising selecting the subsequent motion profile based at least in part on Fisher information associated with the estimate.

10. The method of claim 1, further comprising correcting for lapses in the subject's attention by identifying outlier data and eliminating the outlier data prior to obtaining the first estimate.

11. The method of claim 1, wherein the bias reduced estimate of the fit parameter is obtained iteratively, the method further comprising:
    estimating a second bias quantity for a first bias-reduced estimate; and
    subtracting the second bias quantity from the first bias-reduced estimate to obtain the bias-reduced estimate.

12. A system for assessing a subject's vestibular system, the system comprising:
    a test apparatus for providing a motion profile to a subject and measuring responses of the subject to obtain a set of values as part of a psychometric test the test apparatus comprising:
    a motion platform that includes a device for supporting a subject, wherein the motion platform is configured to execute motion profiles;
    one or more input devices configured to receive the subject's perception of motion;
    a memory; and
    one or more processors programmed to obtain a first estimate of a parameter vector of a psychometric function of the subject based on the subject's perception of motion in response to a first motion profile set, and to adaptively select a subsequent motion profile based at least in part on the first estimate;
    wherein the one or more processors are further configured to:
    determine at least one fit parameter that represents a distribution of the set of values and represents a characteristic of the subject's responses to the psychometric test;
    estimate a bias quantity associated with each said fit parameter;
    subtract the bias quantity from each said fit parameter to obtain a bias-reduced estimate of the fit parameter;
    scale the bias-reduced estimate of the at least one fit parameter by a scale-factor to obtain a final estimate of the fit parameter; and
    generate a quantitative measure representing the subject's vestibular system based on the final estimate of the fit parameter.

13. The system of claim 12, wherein the scale factor has a value substantially equal to or less than one.

14. The system of claim 12, further comprising one or more input devices configured to accept the responses of the subject for stimuli corresponding to a plurality of values of a test parameter associated with the motion profiles, and wherein the responses to different values of the test parameter are scaled using a corresponding scaling function to obtain the set of values.

15. The system of claim 12, further comprising one or more input devices configured to accept the responses of the subject, wherein the responses of the subject are obtained after providing a stimulus to the subject for a predetermined number of times, and wherein a level of the stimulus is associated with a corresponding motion profile.

16. The system of claim 12, wherein the distribution is represented as a cumulative distribution function.

17. The system of claim 12, wherein the at least one fit parameter is determined using a numerical maximum-likelihood method.

18. The system of claim 12, wherein the bias quantity represents a first order asymptotic bias.

19. The system of claim 12, wherein the processor is configured to select the subsequent motion profile to reduce uncertainty in the estimate.

20. The system of claim 12, wherein the processor is configured to select the subsequent motion profile based at least in part on Fisher information associated with the estimate.

21. The system of claim 12, wherein the one or more processors are further configured to correct for lapses in the subject's attention by identifying outlier data and eliminating the outlier data prior to obtaining the first estimate.

22. The system of claim 12, wherein the one or more processors are configured to obtain the bias-reduced estimate iteratively by:
estimating a second bias quantity for a first bias-reduced estimate; and
subtracting the second bias quantity from the first bias-reduced estimate to obtain the bias-reduced estimate.

23. A non-transitory computer readable storage device having encoded thereon computer readable instructions for assessing a subject's vestibular system, which when executed by a processor, cause one or more processors to perform operations comprising:
obtaining a first estimate of a parameter vector of a subject's psychometric function based on the subject's perception of motion in response to a first motion profile set, wherein a psychometric test is administered to the subject by positioning the subject on a motion platform configured to execute motion profiles;
adaptively selecting a subsequent motion profile based at least in part on the first estimate;
obtaining responses of the subject being administered the psychometric test, to obtain a set of values,
determining at least one fit parameter that represents a distribution of the set of values and represents a characteristic of the subject's responses to the psychometric test;
estimating a bias quantity associated with each said fit parameter;
subtracting the bias quantity from each said fit parameter to obtain a bias-reduced estimate of the fit parameter;
scaling the bias-reduced estimate of each said fit parameter by a scale-factor to obtain a final estimate of the fit parameter; and
generating a quantitative measure representing the subject's vestibular system based on the final estimate of the fit parameter.

* * * * *

UNITED STATES PATENT AND TRADEMARK OFFICE
CERTIFICATE OF CORRECTION

PATENT NO. : 9,795,335 B2
APPLICATION NO. : 14/390923
DATED : October 24, 2017
INVENTOR(S) : Daniel Michael Merfeld et al.

It is certified that error appears in the above-identified patent and that said Letters Patent is hereby corrected as shown below:

In the Claims

In Column 41, Line 20, in Claim 1, delete "set wherein" and insert --set, wherein--;

In Column 42, Line 12 (approx.), in Claim 12, delete "test the test" and insert --test, the test--;

In Column 42, Line 20, in Claim 12, delete "a memory" and insert --memory--.

Signed and Sealed this
Thirteenth Day of February, 2018

Andrei Iancu
*Director of the United States Patent and Trademark Office*